US012790609B2

(12) United States Patent
Lin et al.

(10) Patent No.: US 12,790,609 B2
(45) Date of Patent: Nov. 10, 2026

(54) COMPLEX FOR TREATING OPTIC NERVE DISEASE, AND PREPARATION METHOD THEREFOR AND USE THEREOF

(71) Applicant: CHENGDU GENREZE GENE TECHNOLOGY CO., LTD., Chengdu (CN)

(72) Inventors: Yunfeng Lin, Chengdu (CN); Jiajie Li, Chengdu (CN); Xiaoxiao Cai, Chengdu (CN)

(73) Assignee: CHENGDU GENREZE GENE TECHNOLOGY CO., LTD., Chengdu (CN)

( * ) Notice: Subject to any disclaimer, the term of this patent is extended or adjusted under 35 U.S.C. 154(b) by 417 days.

(21) Appl. No.: 18/267,015

(22) PCT Filed: Mar. 14, 2022

(86) PCT No.: PCT/CN2022/080771
§ 371 (c)(1),
(2) Date: Jun. 13, 2023

(87) PCT Pub. No.: WO2022/194109
PCT Pub. Date: Sep. 22, 2022

(65) Prior Publication Data
US 2024/0052347 A1 Feb. 15, 2024

(30) Foreign Application Priority Data
Mar. 18, 2021 (CN) ......................... 202110293024.0

(51) Int. Cl.
*C12N 15/113* (2010.01)
*A61P 25/02* (2006.01)
*A61P 27/06* (2006.01)

(52) U.S. Cl.
CPC ............ *C12N 15/113* (2013.01); *A61P 25/02* (2018.01); *A61P 27/06* (2018.01);
(Continued)

(58) Field of Classification Search
CPC ............ C12N 15/113; C12N 2310/141; C12N 2310/151; C12N 2310/3519; A61P 25/02;
(Continued)

(56) References Cited

U.S. PATENT DOCUMENTS

2019/0046576 A1 2/2019 Gangaraju et al.

FOREIGN PATENT DOCUMENTS

CN 109072189 12/2018
CN 112007044 12/2020
(Continued)

OTHER PUBLICATIONS

Gu, Wei, et al. "Micro RNA-22 regulates inflammation and angiogenesis via targeting VE-cadherin." FEBS letters 591.3 (2017): 513-526.*
(Continued)

*Primary Examiner* — Kimberly Chong
(74) *Attorney, Agent, or Firm* — Gregory P. Einhorn; Greer, Burns & Crain, Ltd.

(57) ABSTRACT

Disclosed is a complex tFNA-miR22 for treating optic nerve disease, which complex is composed of tetrahedral DNA and miR-22 according to a molar ratio of 1:(1-4). The tFNA-miR22 can inhibit apoptosis of retinal ganglion cells and promote the release of a brain-derived neurotrophic factor (BDNF). The tFNA-miR22 can be used for preparing drugs, and for the treatment of neurodegenerative optic nerve diseases including glaucoma.

20 Claims, 46 Drawing Sheets
(31 of 46 Drawing Sheet(s) Filed in Color)
Specification includes a Sequence Listing.

(52) U.S. Cl.
CPC .. *C12N 2310/141* (2013.01); *C12N 2310/151* (2013.01); *C12N 2310/3519* (2013.01)

(58) Field of Classification Search
CPC .... A61P 27/06; A61K 31/7105; A61K 31/711
See application file for complete search history.

(56) References Cited

FOREIGN PATENT DOCUMENTS

| | | | |
|---|---|---|---|
| WO | 2013070821 | A1 | 5/2013 |
| WO | 2018226640 | | 12/2018 |

OTHER PUBLICATIONS

Feng, Liang, and Xiaorong Liu. "NLRP3 inflammasome in retinal ganglion cell loss in optic neuropathy." Neural Regeneration Research 11.7 (2016): 1077-1078.*
Zhang et al. (Nano Lett. 2018, 18, 5652-5659).*
Biousse, Valérie, and Nancy J. Newman. "Diagnosis and clinical features of common optic neuropathies." The lancet neurology 15.13 (2016): 1355-1367.*
Shao et al. ("Effect of tetrahedral DNA nanostructures on osteogenic differentiation of mesenchymal stem cells via activation of the Wnt/β-catenin signaling pathway." Nanomedicine: Nanotechnology, Biology and Medicine 13.5 (2017): 1809-1819).*
Mu et al. "Correlation between NLRP3 inflammation complex and the degree of optic nerve injury in primary glaucoma" Int Eye Sci, 2019, v 19, n 7, p. 1123-1125, Abstract only.
Romano et al., "MicroRNA target prediction in glaucoma" Progress in Brain Research, Dec 31, 2019, v 220, p. 217-240.
Zhang et al., "Design, fabrication and applications of tetrahedral DNA nanostructure-based multifunctional complexes in drug delivery and biomedical treatment" Nature Protocols, Aug. 15, 2020, v 7, n 15, p. 2728-2757.
Mou et al. "Correlation between NLRP3 inflammation complex and the degree of optic nerve injury in primary glaucoma", (International Journal of Ophthalmology, Jul. 31, 2019, pp. 1123-1125, vol. 19, No. 7.
Huet al., "Protective effects of microRNA-22-3p against retinal pigment epithelial inflammatory damage by targeting NLRP3 inflammasome" Journal of Cellular Physiology, Dec 31, 2019, v 234, p. 18849-18857.

* cited by examiner a. TEM tFNA-miR22

Fig.10A-B
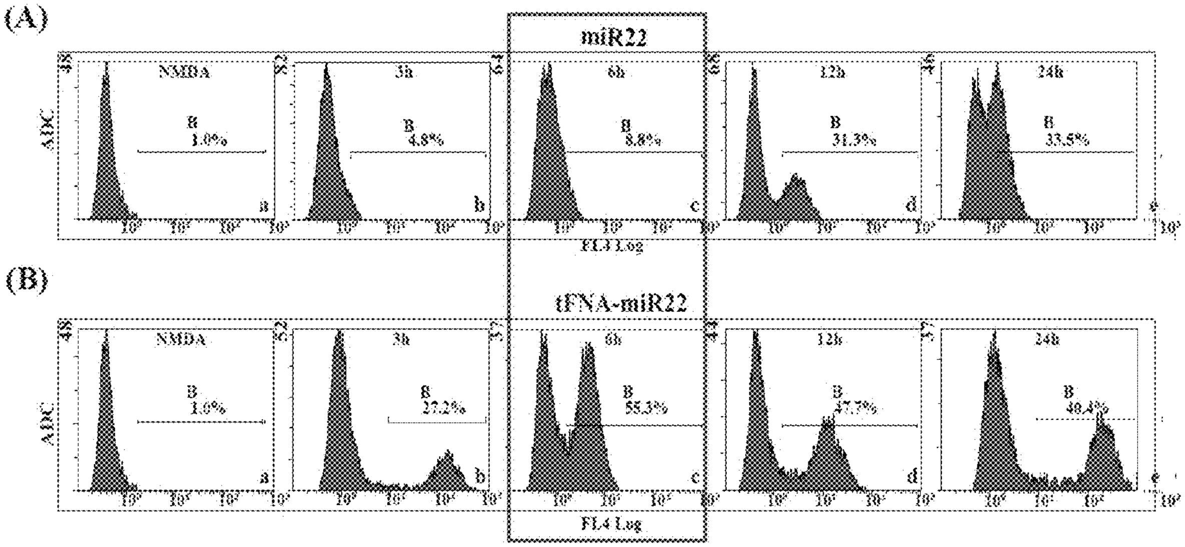

Fig.12G g

| Group / Cell circle | Control | NMDA | miR22 | tFNA | tFNA-miR22 |
| --- | --- | --- | --- | --- | --- |
| G0 -G1 | 47.68 ± 3.65 | 57.8 ± 5.25 | 56.33 ± 4.36 | 58.06 ± 3.69 | 44.74 ± 2.99 |
| S | 10.45 ± 1.83 | 11.31 ± 0.42 | 14.55 ± 1.90 | 15.97 ± 0.99 | 11.72 ± 4.01 |
| G2 -M | 41.52 ± 5.08 | 30.16 ± 5.14 | 28.54 ± 2.57 | 25.22 ± 2.89 | 42.82 ± 2.24 |

FIG. 13D
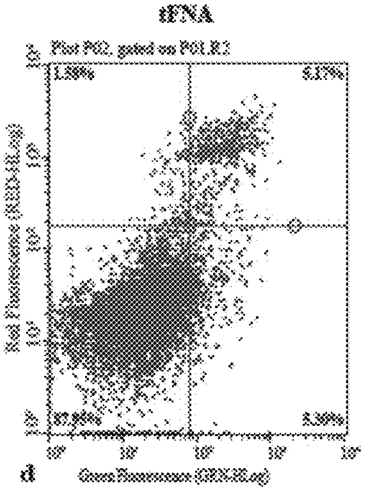
FIG. 13E
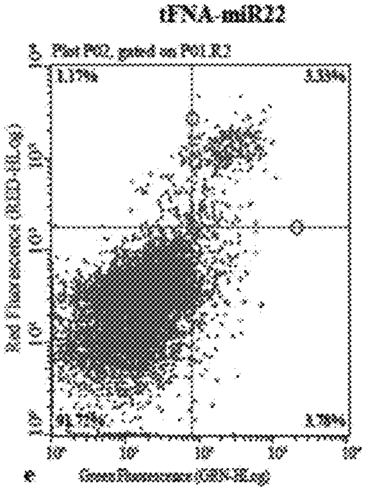
FIG. 13F
| [illegible] | 1 | 2 | 3 | 4 |
|---|---|---|---|---|
| [illegible] | 0.40% ± 0.045 | 3.22% ± 0.351 | 91.62% ± 0.587 | 4.68% ± 0.171 |
| [illegible] | 3.80% ± 1.690 | 11.06% ± 2.985 | 83.40% ± 5.328 | 6.08% ± 0.621 |
| [illegible] | 1.05% ± 0.435 | 4.785% ± 0.380 | 90.00% ± 1.674 | 5.26% ± 0.845 |
| [illegible] | 1.00% ± 0.686 | 4.83% ± 1.625 | 89.01% ± 2.780 | 5.18% ± 0.469 |
| [illegible] | 0.92% ± 0.384 | 3.15% ± 0.151 | 91.93% ± 0.350 | 4.02% ± 0.196 |
f (A)

SEQUENCE LISTING

<160> NUMBER OF SEQ ID NOS: 6

<210> SEQ ID NO 1
<211> LENGTH: 63
<212> TYPE: DNA
<213> ORGANISM: Artificial Sequence
<220> FEATURE:
<223> OTHER INFORMATION: Synthetic

<400> SEQUENCE: 1
atttatcacc cgccatagta gacgtatcac caggcagttg agacgaacat tcctaagtct 60
gaa 63

<210> SEQ ID NO 2
<211> LENGTH: 63
<212> TYPE: DNA
<213> ORGANISM: Artificial Sequence
<220> FEATURE:
<223> OTHER INFORMATION: Synthetic

<400> SEQUENCE: 2
acatgcgagg gtccaatacc gacgattaca gcttgctaca cgattcagac ttaggaatgt 60
tcg 63

<210> SEQ ID NO 3
<211> LENGTH: 63
<212> TYPE: DNA
<213> ORGANISM: Artificial Sequence
<220> FEATURE:
<223> OTHER INFORMATION: Synthetic

<400> SEQUENCE: 3
actactatgg cgggtgataa aacgtgtagc aagctgtaat cgacgggaag agcatgccca 60
tcc 63

<210> SEQ ID NO 4
<211> LENGTH: 63
<212> TYPE: DNA
<213> ORGANISM: Artificial Sequence
<220> FEATURE:
<223> OTHER INFORMATION: Synthetic

<400> SEQUENCE: 4
acggtattgg accctcgcat gactcaactg cctggtgata cgaggatggg catgctcttc 60
ccg 63

<210> SEQ ID NO 5
<211> LENGTH: 22
<212> TYPE: RNA
<213> ORGANISM: Artificial Sequence
<220> FEATURE:
<223> OTHER INFORMATION: Synthetic

<400> SEQUENCE: 5
aagcugccag uugaagaacu gu 22

<210> SEQ ID NO 6
<211> LENGTH: 90
<212> TYPE: DNA
<213> ORGANISM: Artificial Sequence
<220> FEATURE:
<223> OTHER INFORMATION: Synthetic

<400> SEQUENCE: 6

-continued

```
aagctgccag ttgaagaact gttttttact actatggcgg gtgataaaac gtgtagcaag    60

ctgtaatcga cgggaagagc atgcccatcc                                    90
```

COMPLEX FOR TREATING OPTIC NERVE DISEASE, AND PREPARATION METHOD THEREFOR AND USE THEREOF

RELATED APPLICATIONS

This application is a national phase application claiming benefit of priority under 35 U.S.C. § 371 to International (PCT) Patent Application serial number PCT/CN2022/080771, filed Mar. 14, 2022, which claims benefit of priority to Chinese Patent Application No. CN 202110293024.0, filed Mar. 18, 2021. The aforementioned applications are expressly incorporated herein by reference in their entirety and for all purposes.

REFERENCE TO SEQUENCE LISTING

This application includes an electronically submitted sequence listing in .txt format. The .txt file contains a sequence listing entitled "1238-152503_ST25.txt" created on Apr. 9, 2026 and is 1,911 bytes in size. The sequence listing contained in this .txt file is part of the specification and is hereby incorporated by reference herein in its entirety.

FIELD OF THE INVENTION

The invention belongs to the field of biomedicine, and in particular relates to a complex for the treatment of optic nerve diseases and its preparation method and use.

BACKGROUND OF THE INVENTION

Glaucoma is a group of diseases that threaten and injure the optic nerve and its visual pathways and thus lead to visual dysfunction, and is the leading cause of irreversible blindness worldwide. Primary open-angle glaucoma is a specific type of optic nerve disease characterized by progressive injury to the retinal ganglion cells (RGCs) and their axons, with characteristic optic nerve atrophy and visual field defects. Glaucoma tends to be insidious and progresses slowly, with no obvious symptoms in the early stages and the visual field gradually shrinking until blindness. There are nearly 21 million glaucoma patients in China, which will likely produce nearly 6.3 million blind people and over 10 million visually impaired people.

Currently, the main treatment for glaucoma is to reduce intraocular pressure (IOP) medically or surgically to slow down the injure to the optic nerve. However, lowering intraocular pressure alone cannot completely and effectively prevent or reverse optic nerve injury caused by retinal ganglion cell death. In some glaucoma patients, the injury of retinal ganglion cells continues to progress even after the intraocular pressure is controlled, and vision may be completely lost if no effective treatment is taken.

Optic nerve protection has been a frontier hot spot in ophthalmology research in recent years, as well as a difficult point in the treatment of glaucoma. At present, the commonly used drugs in clinical practice, such as prostaglandins, β-receptor blockers, adrenergic agonists, carbonic anhydrase inhibitors, and myotic agents including pilocarpine are all ocular hypotensive agents, while neuroprotective drugs are scarce.

Tetrahedral DNA (TDN), also known as tetrahedral framework nuclear acids (tFNAs) and tetrahedral DNA nanostructures, is a tetrahedral nanostructure formed by 4 single-stranded DNAs through denaturation and renaturation, with complementary base pairing between the strands.

It is easy to synthesize and has high biocompatibility, and is usually used as a carrier for certain drugs. Chinese patent application CN109806275A discloses the use of tetrahedral DNA to promote the proliferation, differentiation and/or migration of neural stem cells, but does not disclose the effect of tetrahedral DNA on the protection of optic nerve. CN112007044A discloses the use of tetrahedral DNA for the preparation of drugs to prevent oxidative stress in retinal ganglion cells, showing that tetrahedral DNA alone or its complex with miR-155 can be used for the treatment of wet macular degeneration (AMD).

As one of the most frequently studied microRNAs, miR-22 is involved in a variety of biological processes such as cardiac remodeling, cell cycle regulation, proliferation, and differentiation, and has various anti-neurodegenerative and anti-tumor effects, including inhibition of neuronal apoptosis and participation in the regulation of brain-derived neurophilic factor (BDNF)-related signaling pathways, and inhibition of proliferation, invasion, and migration of a variety of tumor cells. Romano et al. revealed that miR-22 is a target gene for predicting glaucoma, but the use of miR-22 as a target gene for treating glaucoma has not been disclosed (Romano G L, Platania C B, Forte S, Salomone S, Drago F, Bucolo C. MicroRNA target prediction in glaucoma. Prog Brain Res. 2015; 220:217-40.).

In summary, there are still no reports on the use of tetrahedral DNA or miR-22 in the treatment of glaucoma, let alone the combined use of the two as optic neuroprotective drugs in the treatment of glaucoma. In order to overcome the difficulties in the treatment of glaucoma, it is urgent to further develop neuroprotective drugs that can effectively treat optic nerve diseases.

SUMMARY OF THE INVENTION

The object of the present invention is to provide a drug for the treatment of optic nerve diseases.

The present invention provides a complex for the treatment of optic nerve diseases, which is composed of the tetrahedral DNA and miR-22 according to the molar ratio of 1:(1~4).

The tetrahedral DNA of the present invention is a three-dimensional DNA nanostructure with a tetrahedral shape, which is formed by DNA sequence design, complementary pairing principle and automatic hybridization combination of each strand. In the present invention, four single-stranded DNAs have the nucleotide sequences as shown in SEQ ID NO. 1~SEQ ID NO. 4. A complex of tetrahedral DNA and microRNA is formed by linking a microRNA to an end of the single strand of the tetrahedral DNA. In the present invention, the specific microRNA is miR-22.

Further, the tetrahedral DNA is formed by 4 single-stranded DNAs through complementary base pairing; the 4 single-stranded DNAs have the sequences selected one-to-one from the sequences as shown in SEQ ID NO. 1~4, respectively; wherein the end of one or two or three or each of the single-stranded DNAs is linked to miR-22; miR-22 has the sequence as shown in SEQ ID NO. 5.

Further, the above-mentioned miR-22 is linked to 1~4 single-stranded DNAs of the four single-stranded DNAs forming the tetrahedral DNA structure by a chemical bond or chemical bonds.

Further, there is a linker sequence between miR-22 and the single-stranded DNA(s). The linker sequence is a nucleotide sequence, preferably a deoxyribonucleotide sequence, more preferably -TTTTT-.which is a sequence of 5 consecutive thymine deoxynucleotides.

The present invention also provides a method for the preparation of the above-mentioned complex, wherein 4 single-stranded DNAs of the tetrahedral DNA are maintained at a temperature sufficient to denature them for more than 10 min, and then the temperature is lowered to 2~8° C., maintaining for more than 20 min; and one or more of the 4 single-stranded DNAs as mentioned above is linked to miR-22.

Further, the 4 single strands of the tetrahedral DNA are maintained at 95° C. for 10 min, and then the temperature is lowered to 4° C., maintaining for 20 min.

The present invention also provides the use of the above-mentioned complex in the preparation of a medicament for treating optic nerve disease. Further, the above-mentioned medicament for the treatment of optic nerve diseases is an optic neuroprotective drug; preferably, the optic nerve disease is associated with retinal ganglion cell injury, and/or retinal ganglion cell apoptosis. The drug can slow retinal ganglion cell injury, reduce retinal ganglion cell apoptosis and promote retinal ganglion cell survival; more preferably, the said retinal nerve disease is associated with brain-derived neurological factor (BNDF)-related signaling pathways, and the drug can promote the release of BDNF.

Further, the optic nerve disease is glaucoma; and in particular, primary open angle glaucoma.

The present invention also provides a pharmaceutical composition for the treatment of optic nerve diseases, which comprises the above-mentioned complex for the treatment of optic nerve diseases and pharmaceutically acceptable excipients.

The present invention also provides a method for the treatment and/or prevention of optic nerve diseases, comprising administering an effective amount of the complex of tetrahedral DNA and miR-22 of the present invention or the pharmaceutical composition of the present invention to a patient in need thereof. The optic nerve disease is preferably glaucoma.

The experimental results show that tFNA-miR22, a complex of tetrahedral DNA and miR-22 of the present invention, can effectively inhibit apoptosis of retinal ganglion cells induced by N-methyl-D-aspartate (NMDA) and promote the release of brain-derived neurophilic factor (BDNF), so as to play a good protective effect on retinal ganglion cells. The application of tFNA-miR22 for the preparation of an optic nerve protective drug will be helpful for the treatment of neurodegenerative optic nerve diseases including glaucoma, which has a very good application prospect.

Obviously, according to the above contents of the present invention, other various forms of modifications, replacements or alterations can be made in accordance with the general technical knowledge and conventional means in the field, without departing from the above basic technical ideas of the present invention.

The above contents of the present invention will be further described in detail by means of specific embodiments in the form of examples. However, it should not be construed as limiting the scope of the above-mentioned subject matter of the present invention to the following examples. All technologies implemented based on the above contents of the invention belong to the scope of the invention.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A-B: CCK-8 activity detection, cell viability (FIG. 6B) and drug inhibition (FIG. 6A) rates of the cells which were stimulated by different concentrations of NIDA for 1 h and cultured in complete medium for 3, 6, 12, and 24 h;

FIG. 6C: biosafety detection of tFNA-miR22;

FIG. 6D: CCK-8 activity detection of cells which were treated with 4 nM NMDA and then treated with different concentrations of tFNA-miR22, tetrahedral DNA and single-stranded miR-22 for 24 h;

FIG. 6E: illustrates an image of cell morphology in each group after the above treatment under ordinary light microscope; and Data from FIG. 6A-D refer to mean±standard deviation (with sample size of each group ≥3).

FIG. 8A-E shows the results of hematoxylin-eosin staining of: FIG. 8A illustrates staining of the control section; 8B illustrates staining of the NMDA test section; 8C illustrates staining of the miR22 test section; 8D illustrates staining of the tFNA test section; and FIG. 8E illustrates staining of the tFNA-miR22 test section;

FIG. 10A-B shows the results of the cell penetration rate of tFNA-miR22 (FIG. 10B) and single-stranded miR-22 (FIG. 10A) (Cy5 fluorescent-labeled) within 3, 6, 12 and 24 h detected by flow cytometry.

FIG. 12A-G illustrate the effect of 62.5 nM tFNA-miR22, tetrahedral DNA and single-stranded mi-R22 on cell cycle detected by flow cytometry and data analysis, FIG. 12A graphically illustrates the flow cytometry control data, FIG. 12B graphically illustrates the flow cytometry e NMDA test data, FIG. 12C graphically illustrates the flow cytometry miR22 test data, FIG. 12D graphically illustrates the flow cytometry tFNA test data, FIG. 12E graphically illustrates the flow cytometry tFNA-miR22 test data, FIG. 12F graphically illustrates a summary of the test data, FIG. 12G illustrates a table summarizing the test data, and, the statistical data refer to mean±standard deviation (with sample size of each group ≥3).

FIG. 13A-F illustrate the apoptosis of cells in each group detected by flow cytometry and statistical data analysis, FIG. 13A graphically illustrates the flow cytometry control data, FIG. 13B graphically illustrates the flow cytometry NMDA test data, FIG. 13C graphically illustrates the flow cytometry miR22 test data, FIG. 13D graphically illustrates the flow cytometry tFNA test data, FIG. 13E graphically illustrates the flow cytometry tFNA-miR22 test data, FIG. 13F illustrates a table summarizing the test data, and, the statistical data refer to mean±standard deviation (with sample size of each group ≥3).

FIG. 14A illustrates the expression of apoptosis-related proteins detected by Western blot;

FIG. 14B graphically illustrates statistical analysis of anti-apoptotic protein Bcl-2;

FIG. 14C graphically illustrates statistical analysis of apoptotic protein Bax; and FIG. 14D graphically illustrates statistical analysis of apoptotic protein Caspase-3.

FIG. 18A illustrates: expression level of TrkB/BDNF protein analyzed by Western blot (GAPDH as internal reference);

FIG. 18B graphically illustrates: relative expression level of TrkB protein;

FIG. 18C graphically illustrates: relative expression level of BDNF protein;

FIG. 18D graphically illustrates: expression level of Ntrk2 gene; and

FIG. 18E graphically illustrates: expression level of BDNF gene.

FIG. 19A expression of ERK1/2-CREB protein analyzed by Western blot;

FIG. 19B graphically illustrates relative expression levels of ERK1/2 and phosphorylated ERK1/2 protein; and FIG. 19C graphically illustrates relative expression levels of CREB and phosphorylated CREB proteins;

DETAILED DESCRIPTION OF THE INVENTION

The raw materials and equipment used in the present invention are known products and commercially available.

Example 1. Synthesis of the Complex of tFNA and miR-22 (tFNA-miR22)

Four DNA single strands, one of which was connected to miR22 at its end (S1, S2, S3-miR22, S4), were dissolved in TM Buffer (10 mM Tris-HCl, 50 Mm $MgCl_2$, pH=8.0) at a final concentration of 1000 nM for each of the four DNA single strands, fully mixed, rapidly heated to 95° C., maintaining for 10 min, and then rapidly cooled to 4° C., maintaining for more than 20 min, to obtain tFNA-miR22.

The sequences of the four single strands (5→3') were as follows:

S1:

S1: (SEQ ID NO. 1)
ATTTATCACCCGCCATAGTAGACGTATCACCAGGCAGTTGAGACGAACAT
TCCTAAGTCTGAA

S2: (SEQ ID NO. 2)
ACATGCGAGGGTCCAATACCGACGATTACAGCTTGCTACACGATTCAGAC
TTAGGAATGTTCG

S3: (SEQ ID NO. 3)
ACTACTATGGCGGGTGATAAAACGTGTAGCAAGCTGTAATCGACGGGAAG
AGCATGCCCATCC

S4: (SEQ ID NO. 4)
ACGGTATTGGACCCTCGCATGACTCAACTGCCTGGTGATACGAGGATGGG
CATGCTCTTCCCG

-continued miR-22:

(SEQ ID NO. 5)

AAGCUGCCAGUUGAAGAACUGU

S3-miR22-3p:

(SEQ ID NO. 6)

AAGCUGCCAGUUGAAGAACUGU-TTTTT-ACTACTATGGCGGGTGATAAA

ACGTGTAGCAAGCTGTAATCGACGGGAAGAGCATGCCCATCC

Wherein, the 5' end of S1 was optionally linked to a Cy5 fluorescent label group for tracing tFNA-22.

2. Identification

The DNA single-strands and synthetic tFNA-miR22 were detected by capillary electrophoresis and PAGE electrophoresis. The morphology of tFNA and tFNA-miR22 were detected by transmission electron microscopy. The zeta potential and particle size of tFNA and tFNA-miR22 were detected by dynamic light scattering.

3. Identification Results

Figure 1:
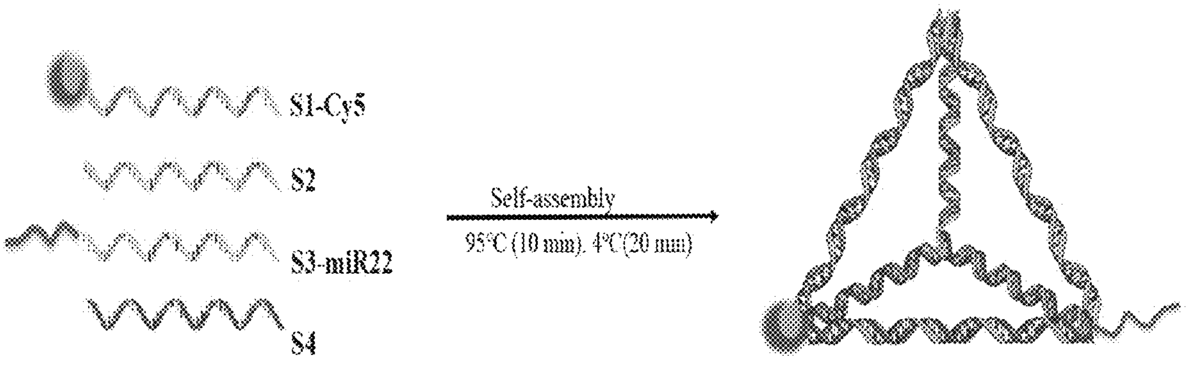
FIG. 1 shows the schematic diagram of the synthesis of tetrahedral DNA and miR-22.
Figure 2:
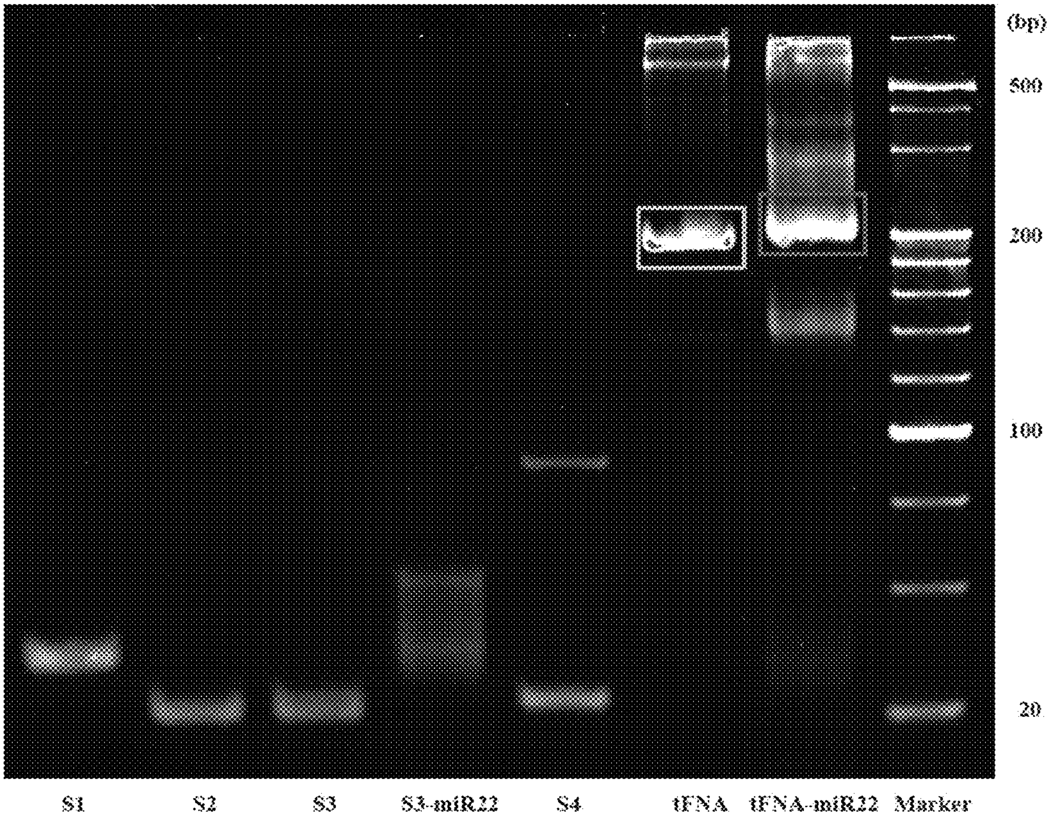
FIG. 2 shows the detection results (including detecting S3-miRNA, tFNA, TFNA-miR22) using capillary electrophoresis.
Figure 3A:
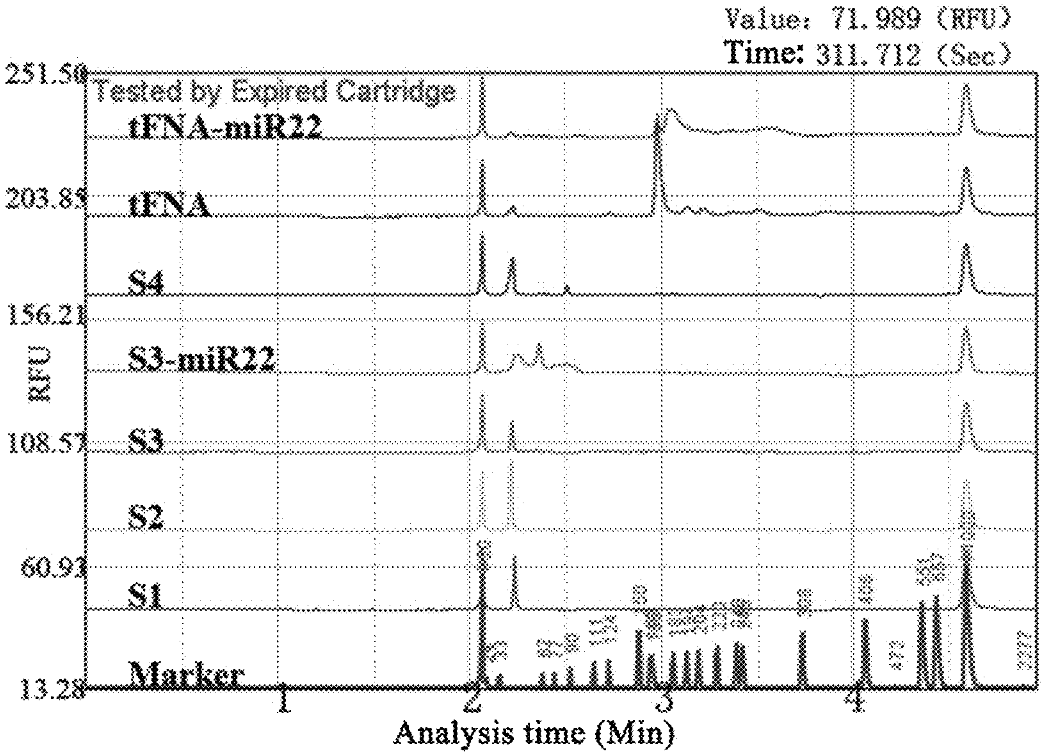
FIG. 3A graphically illustrates the data illustrated in the PAGE electrophoresis of FIG. 3B.
Figure 3B:
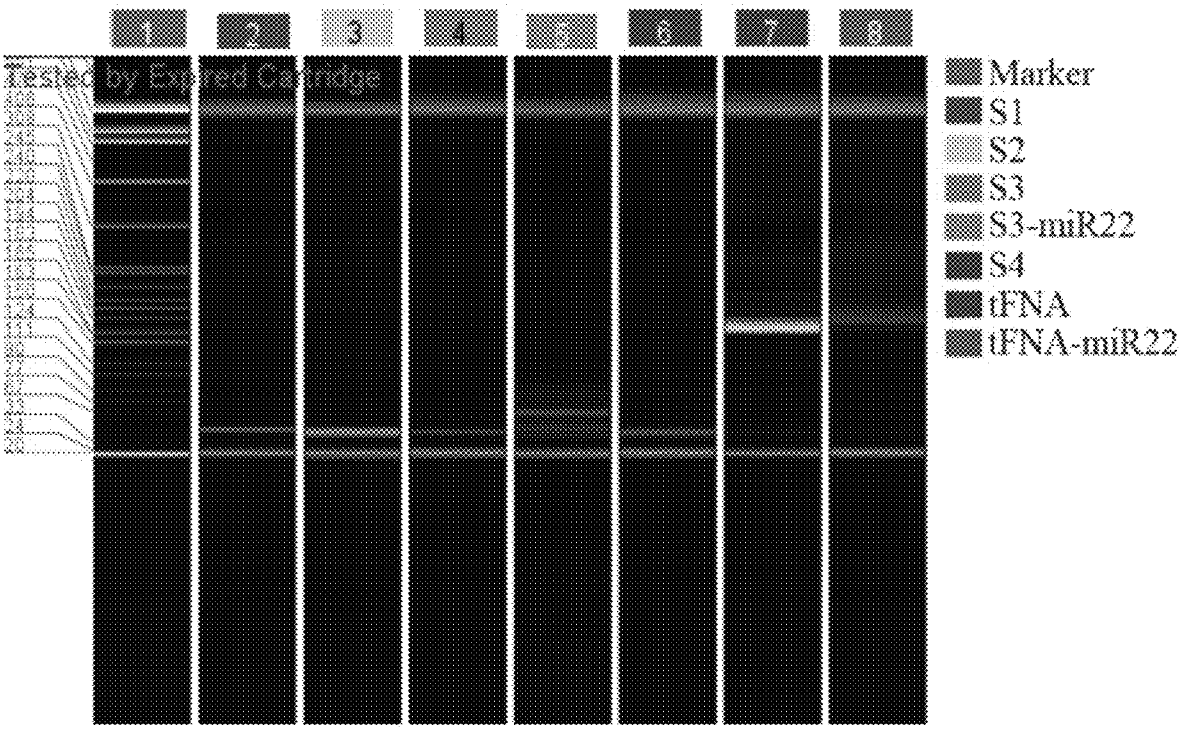
FIG. 3B shows the detection results of PAGE electrophoresis of tFNA-miR22, tetrahedral DNA and its single-strands (1: S1, 2: S2, 3: S3, 4: S3-miR22, 5: S4, 6: tFNA, 7: tFNA-miR22).
Figure 4A:
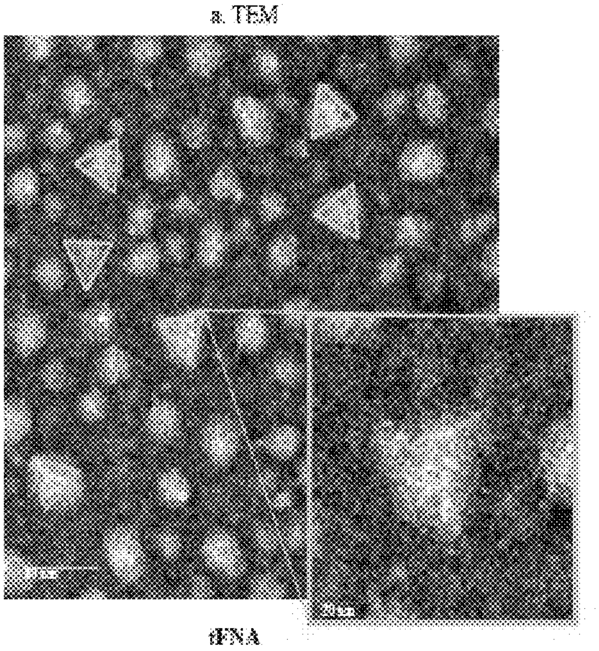
FIG. 4A-B illustrate images of tetrahedral DNA by transmission electron microscopy (FIG. 4A) and atomic force microscope (FIG. 4B), and FIG. 4C-D graphically illustrate detection results of Zeta potential (FIG. 4C) and particle size of tetrahedral DNA (FIG. 4D).
Figure 4B:
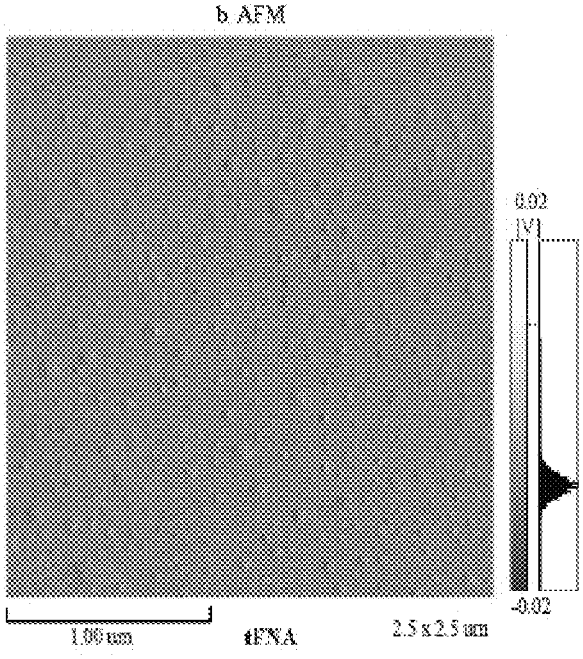
Figure 4C:
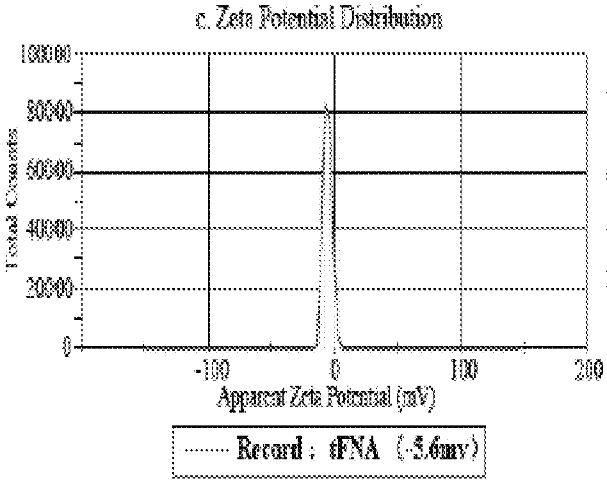
Figure 4D:
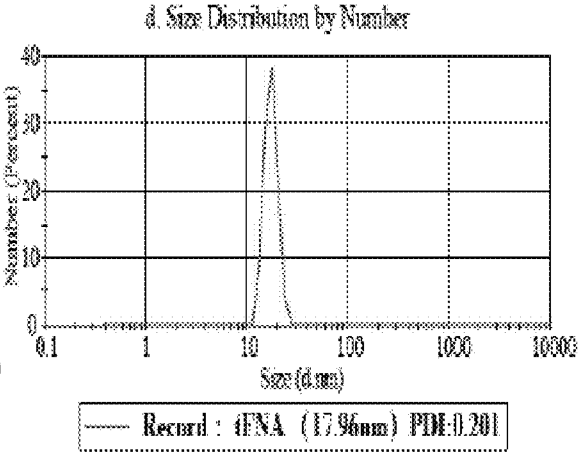
Figure 5A:
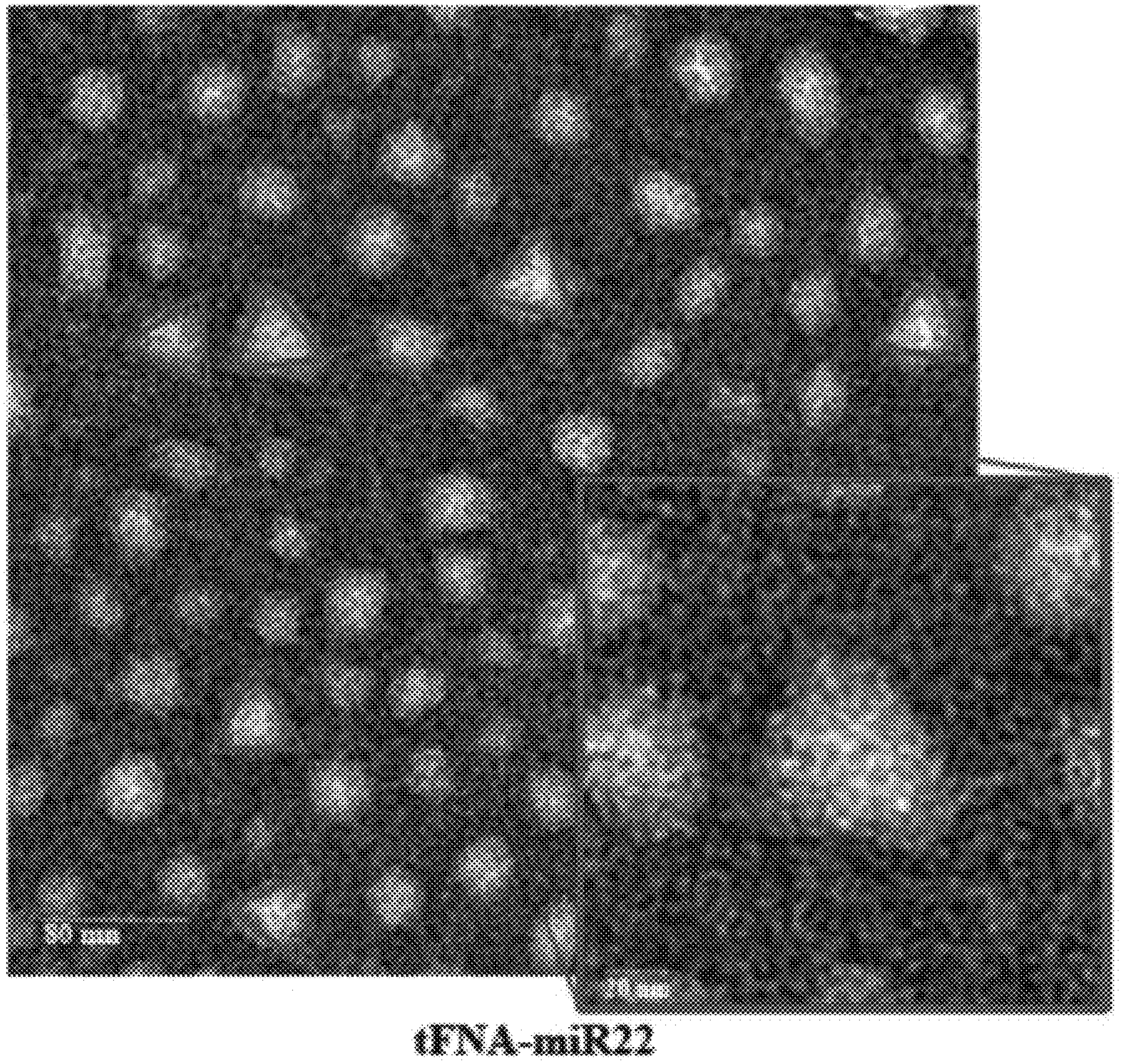
FIG. 5A-B illustrate shows the images of tFNA-miR22 by transmission electron microscopy (FIG. 5A) and atomic force microscope (FIG. 5B), and FIG. 5C-D graphically illustrate detection results of Zeta potential (FIG. 5C) and particle size of tFNA-miR22 (FIG. 5D).
Figure 5B:
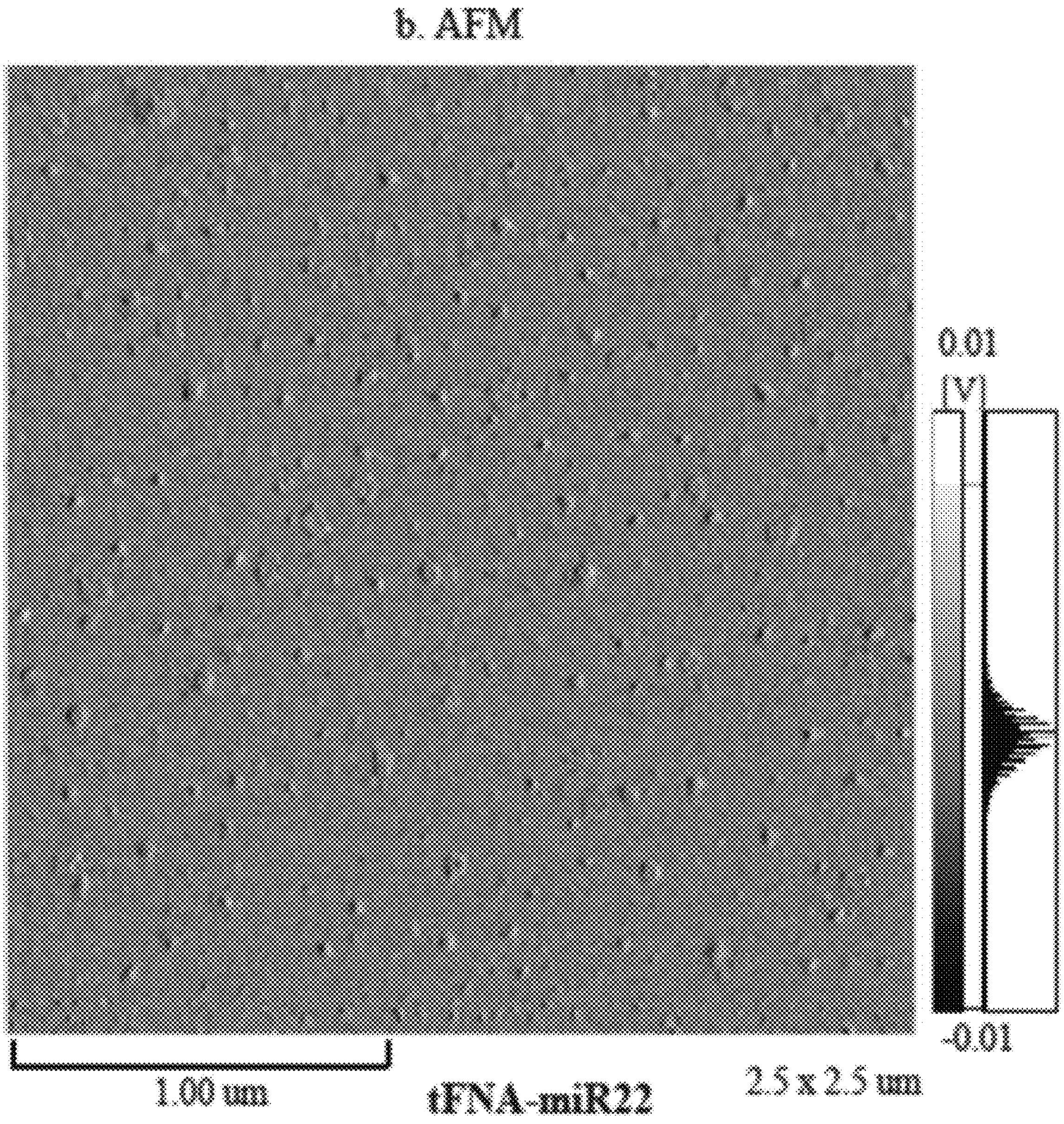
Figure 5C:
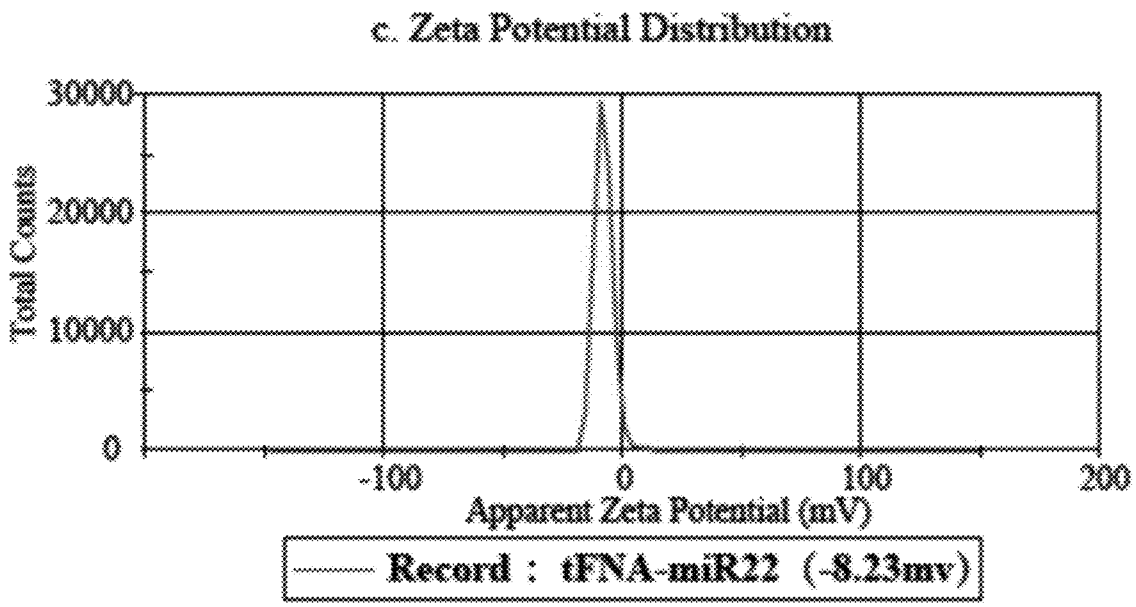
Figure 5D:
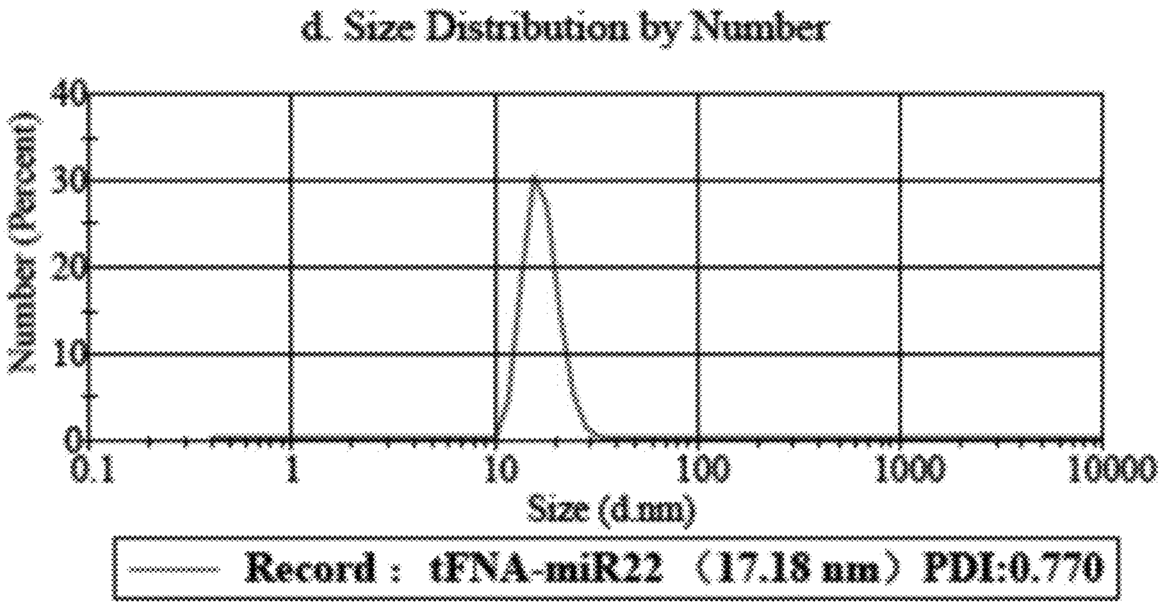

As shown in FIGS. 1-3, the electrophoresis results showed that the molecular weight of tFNA-miR22 band was significantly higher than that of the single-stranded DNAs and the tetrahedral DNA, indicating that the single-stranded DNAs were assembled together.

As shown in FIGS. 4-5, the tetrahedral structure particles were detected by transmission electron microscopy. It was found by dynamic light scattering that the zeta potential of tFNA was 5.6 and the particle size was 17.96 nm; the zeta potential of tFNA-miR22 was 8.23 mV and the particle size was 17.18 nm, indicating that tFNA-miR22 was successfully synthesized and stable.

The beneficial effects of the present invention will be further described by way of experimental examples. The tFNA involved in the experimental examples was prepared by the method of Example 1.

Experimental Example 1. Uptake of tFNA-miR22 by Injured Retinal Ganglion Cells 1. Experimental Methods 1.1 Test of the Optimal Modeling Concentration (In Vitro Simulation of Optic Ganglion Cell Injury)

RGC-5 cells (a type of mouse retinal ganglion cells) were cultured in groups in 96-well plates with $1*10^4$ cells per well. Each group was treated with different concentrations of N-methyl-D-aspartate (NIDA) for 1 h, and then cultured with complete medium for 24 h and then the cell activity was detected by CCK-8 assay. It was found that the drug inhibition rate of 4 mM NMDA was about 40%, so 4 mM was selected as the optimal modeling concentration (FIG. 6: A-B).

1.2 Test of the Optimal Anti-Cell Injury Concentration of Drug (Cell Proliferation Experiment)

RGC-5 cells were cultured in groups in 96-well plates with $1*10^4$ cells per well. Each experimental group except the blank group was treated with 4 nM NMDA for 1 h, and then cultured for another 24 h with a culture medium containing 0 nM, 62.5 nM, 125 nM and 250 nM tFNA and tFNA-miR22 prepared in the example 1, as well as the single-stranded miR-22, respectively. Samples were taken and detected for cell activity by CCK-8 assay. It was found that tFNA at 62.5 nM had no obvious proliferative effect, while tFNA-miR22 at this concentration could significantly promote the proliferation of RGC-5 cells, moreover, the proliferation ratio of the cell viability treated with tFNA-miR22 compared to the cell viability of the NMDA control group was even higher than the sum of the proliferation ratios of the cell viability of miR22 or tFNA alone compared to the cell viability of the NMDA control group, indicating that the combination of miR22 and tFNA into tFNA-miR22 played a synergistic role in promoting the proliferation of NMDA-injured ganglion cells. Therefore, 62.5 nM was selected as the optimal drug concentration for this experiment. (FIG. 6: D).

1.3 Test of Material Uptake by Injured Cells

Figure 11:
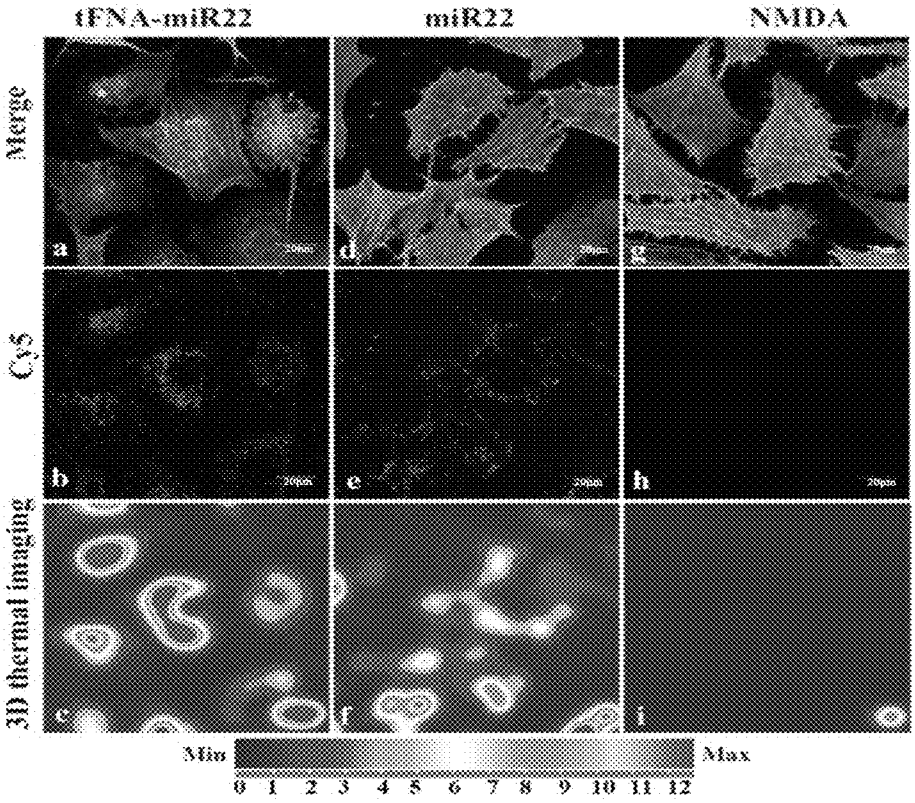
FIG. 11 shows immunofluorescence images of the uptake results of tFNA-miR22 and single-stranded miR-22 (Cy5 fluorescent-labeled) for 6 h detected by the immunofluorescence.
Figure 12A:
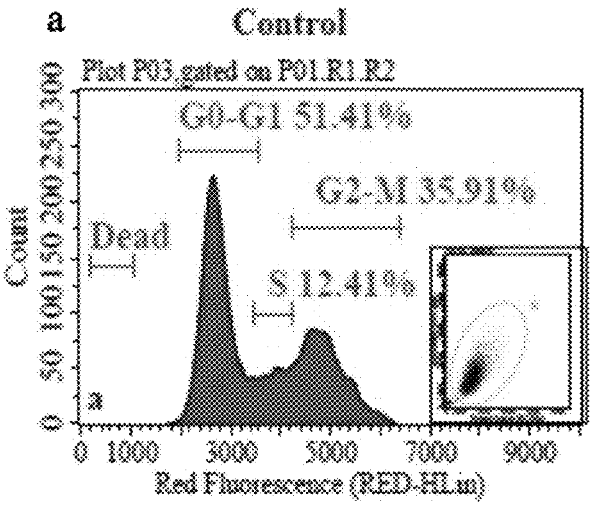
Figure 12B:
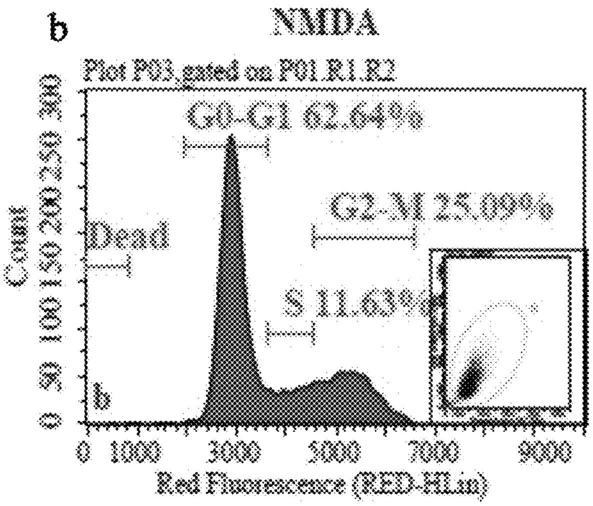
Figure 12C:
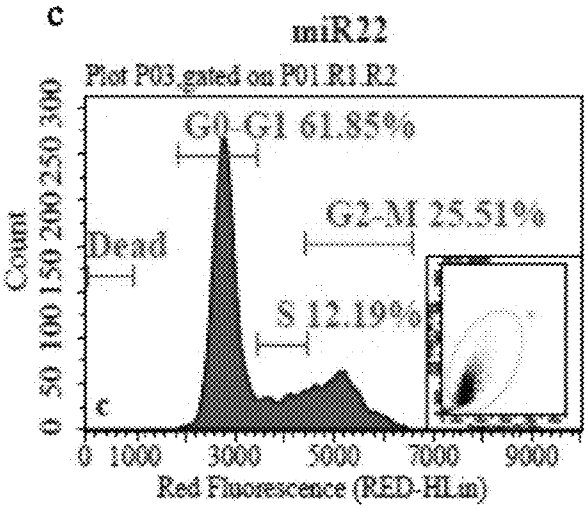
Figure 12D:
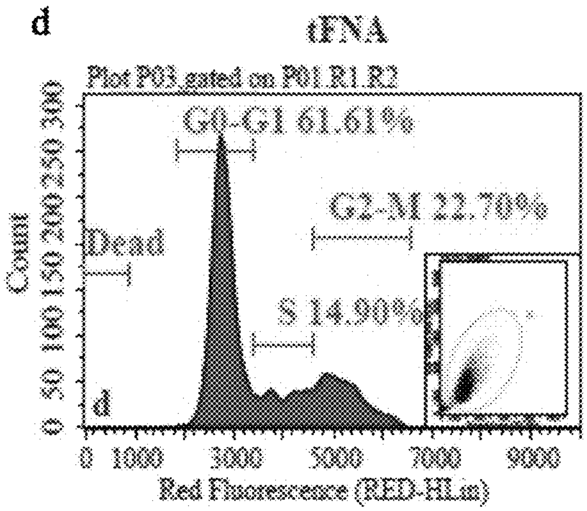
Figure 12E:
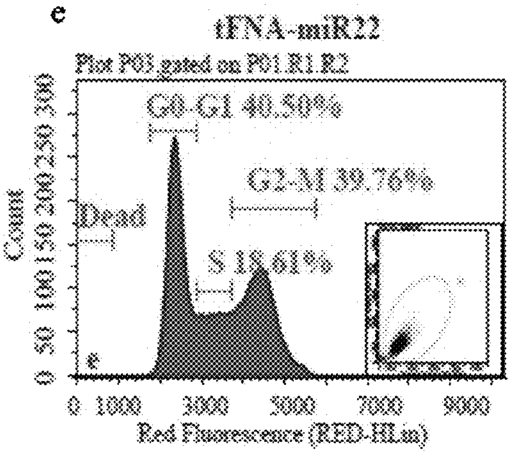
Figure 12F:
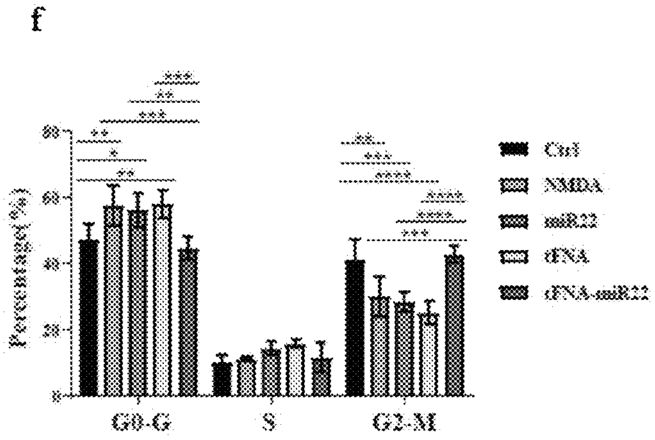
Figure 13A:
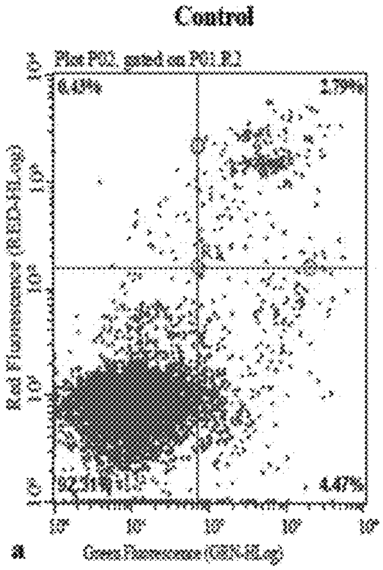
Figure 13B:
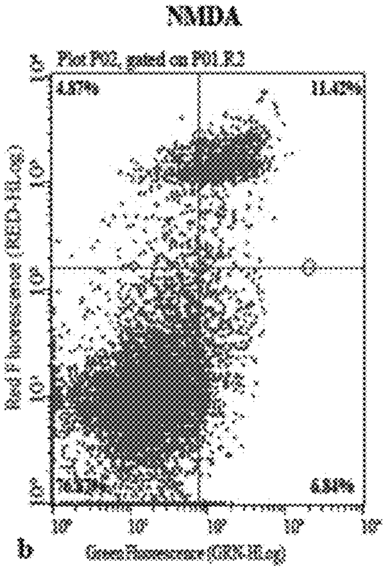
Figure 13C:
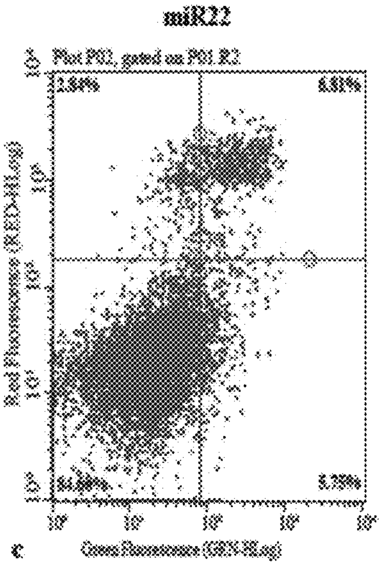
Figure 14A:
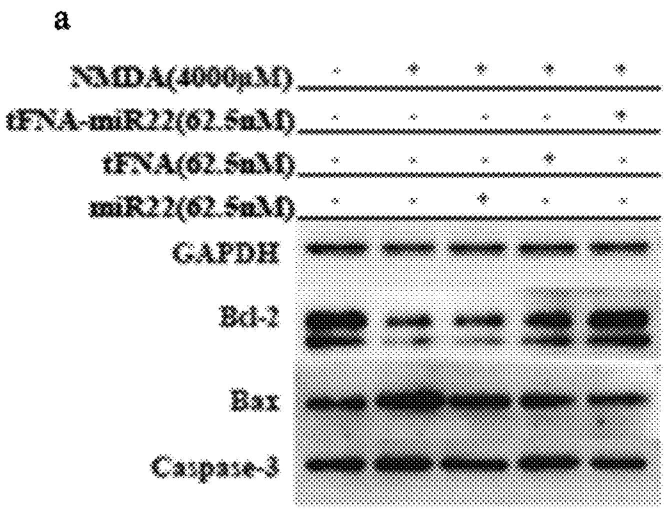
FIG. 14A-D illustrate.
Figure 14B:
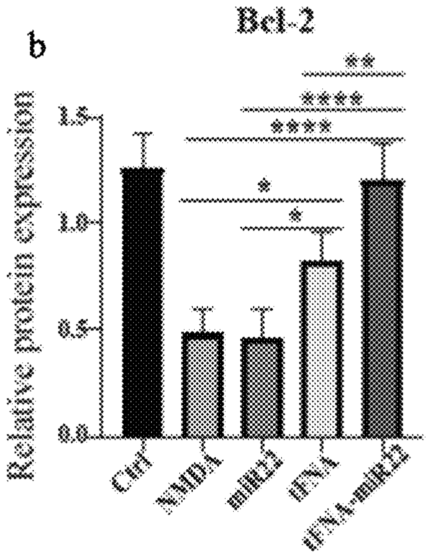
Figure 14C:
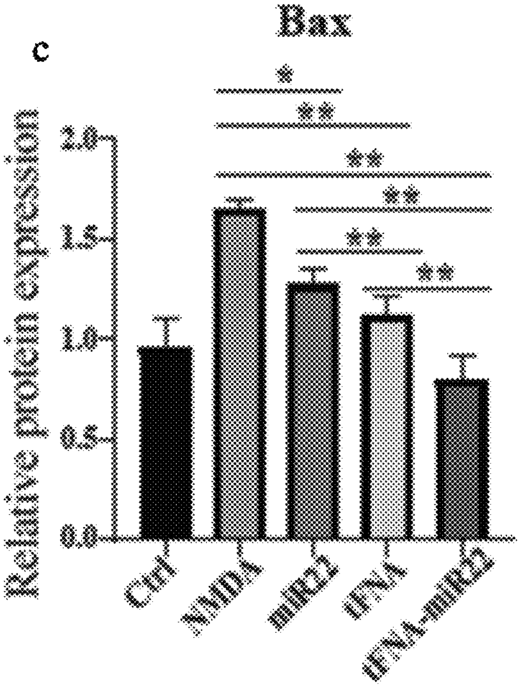
Figure 14D:
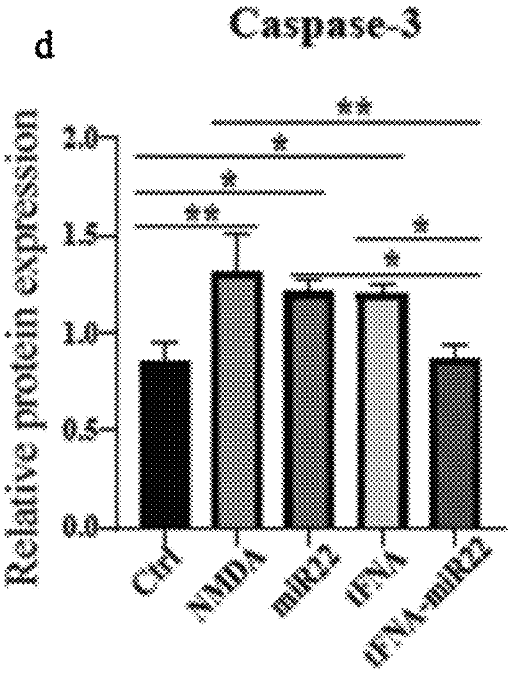
Figure 15A:
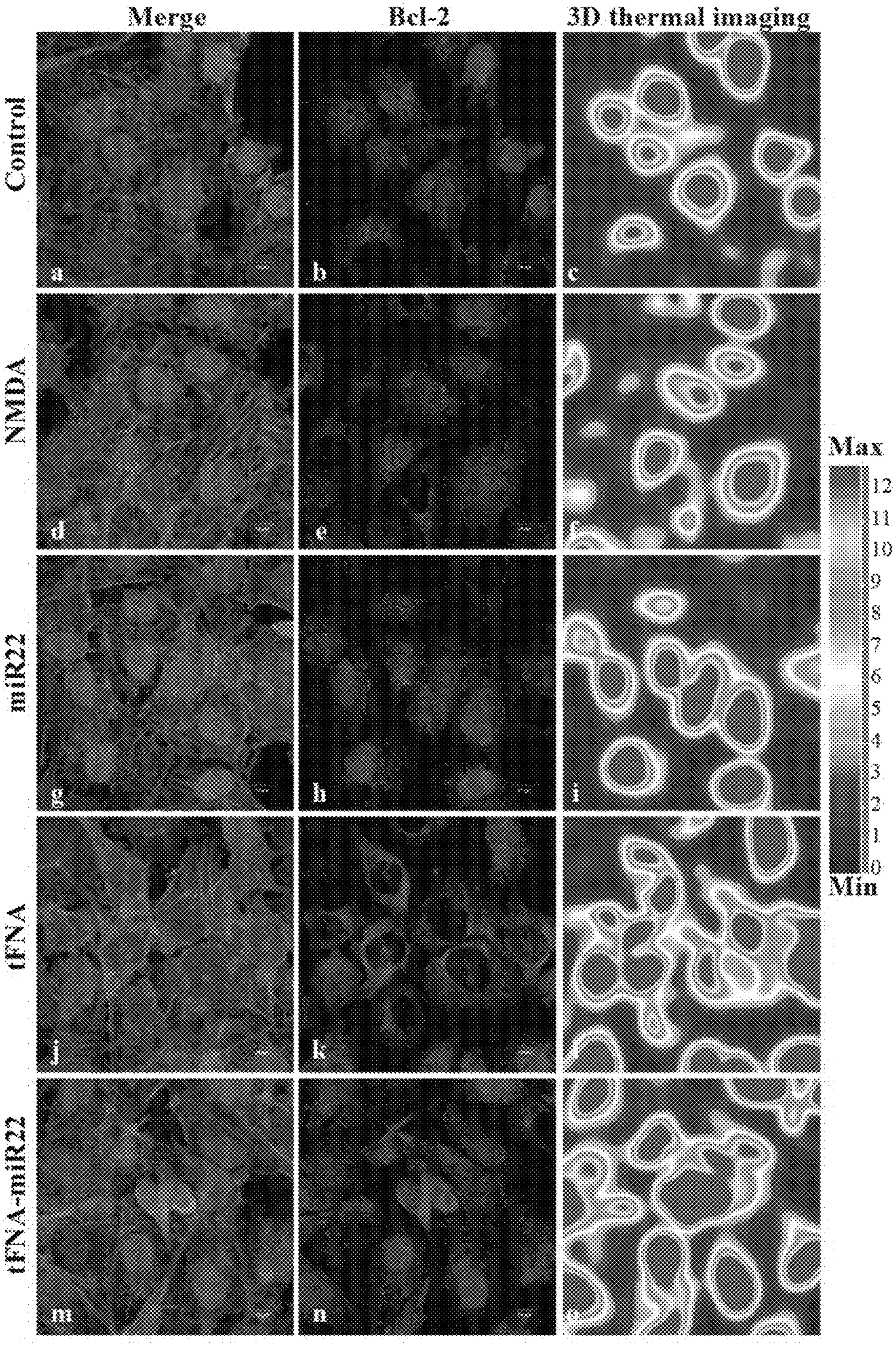
FIG. 15A-B illustrate the immunofluorescence staining (FIG. 15A) of anti-apoptotic protein Bcl-2, and FIG. 15B graphically illustrates a mean fluorescence intensity, and statistical analysis.
Figure 15B:
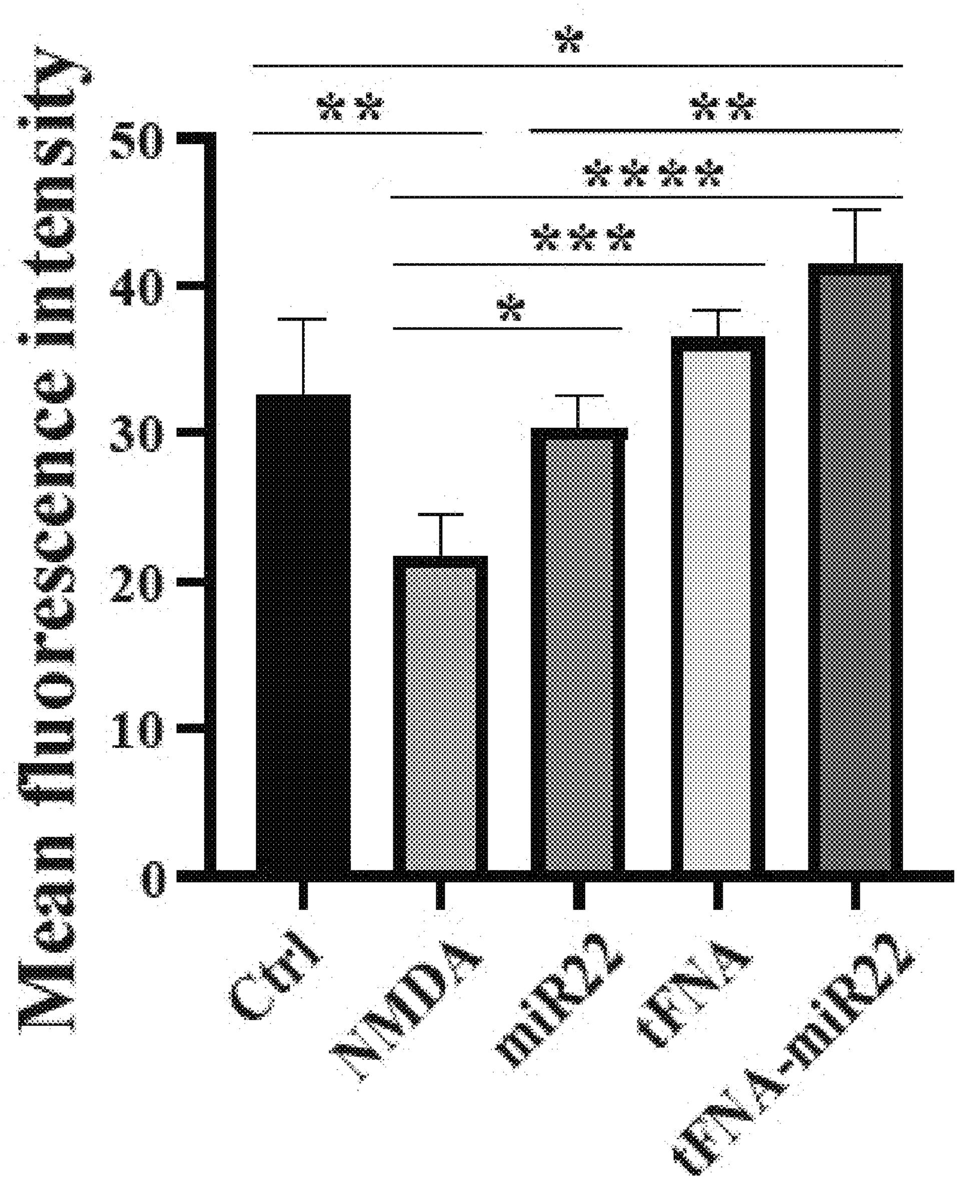
Figure 16A:
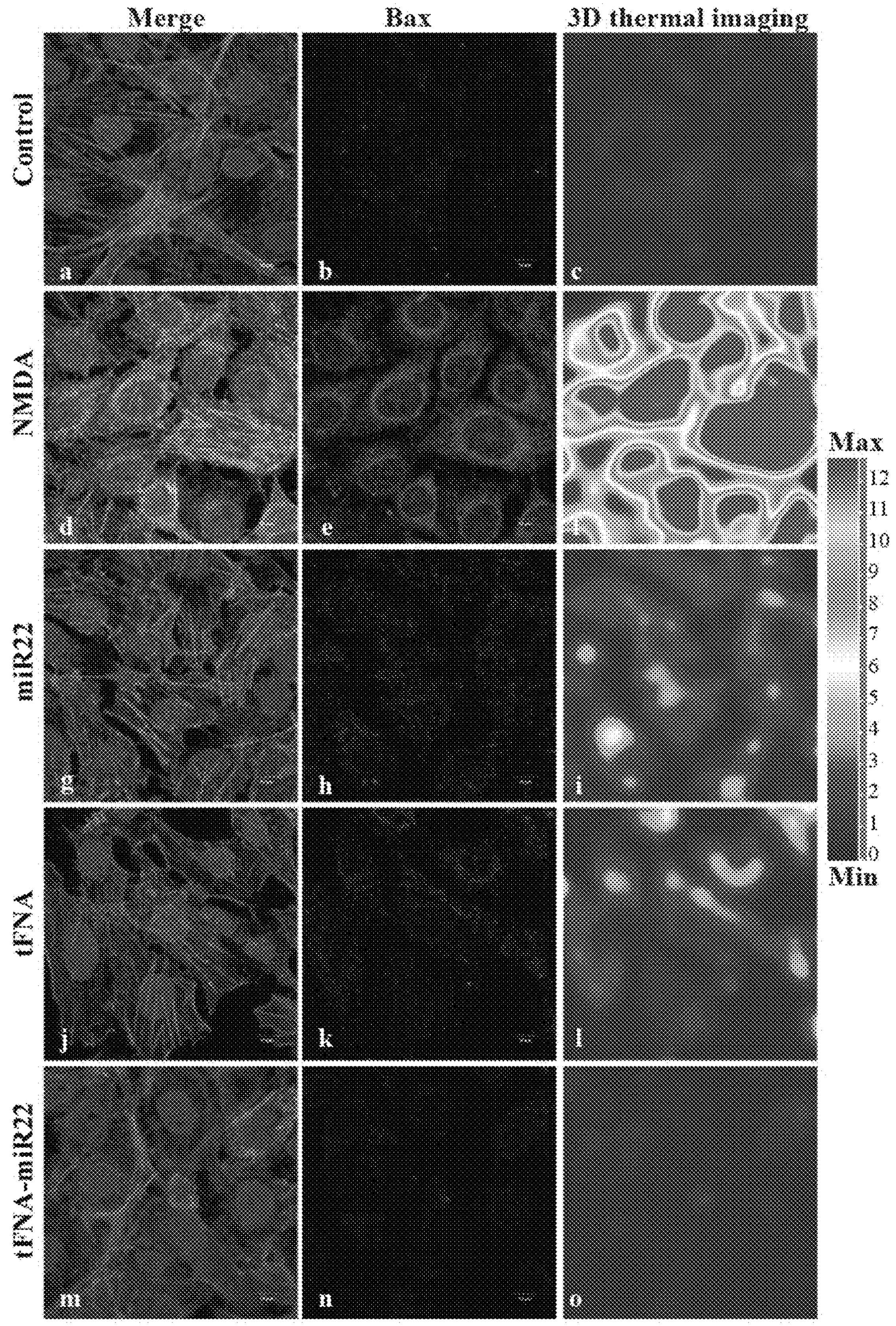
FIG. 16A-B illustrate the immunofluorescence staining (FIG. 16A) of apoptosis protein Bax, and FIG. 16B graphically illustrates a mean fluorescence intensity, and statistical analysis.
Figure 16B:
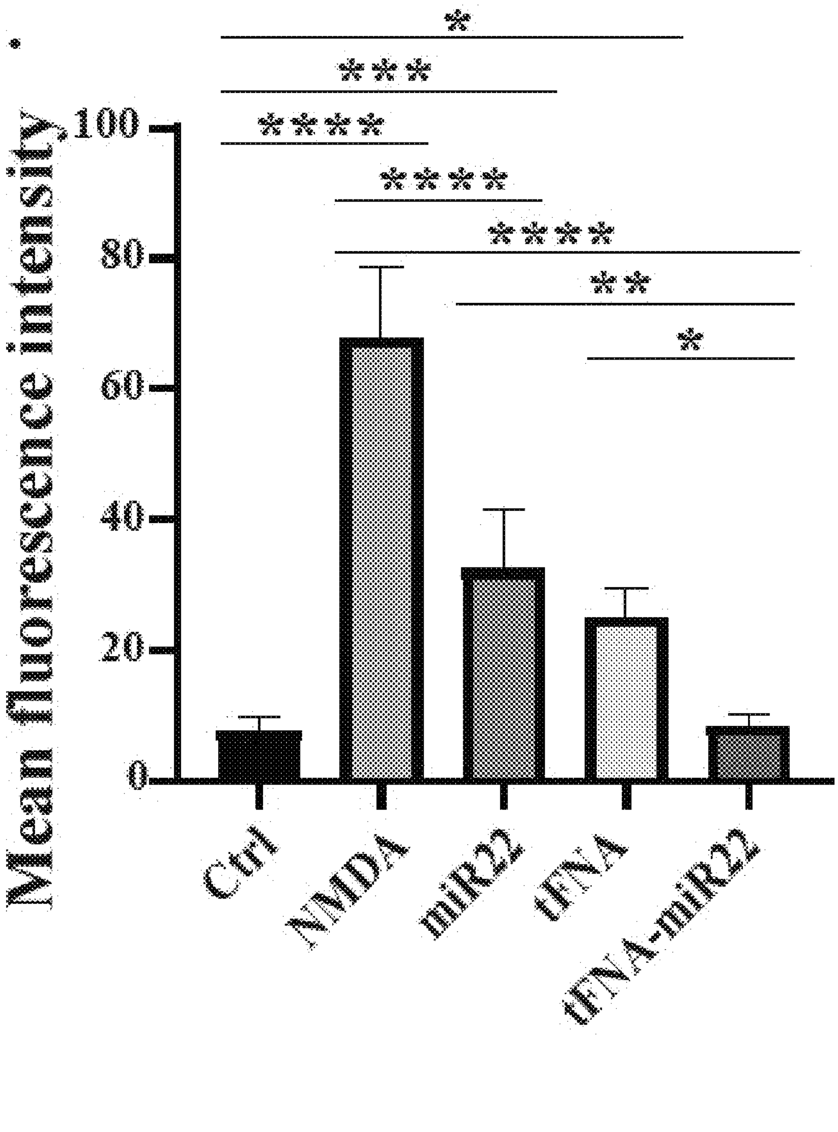
Figure 17A:
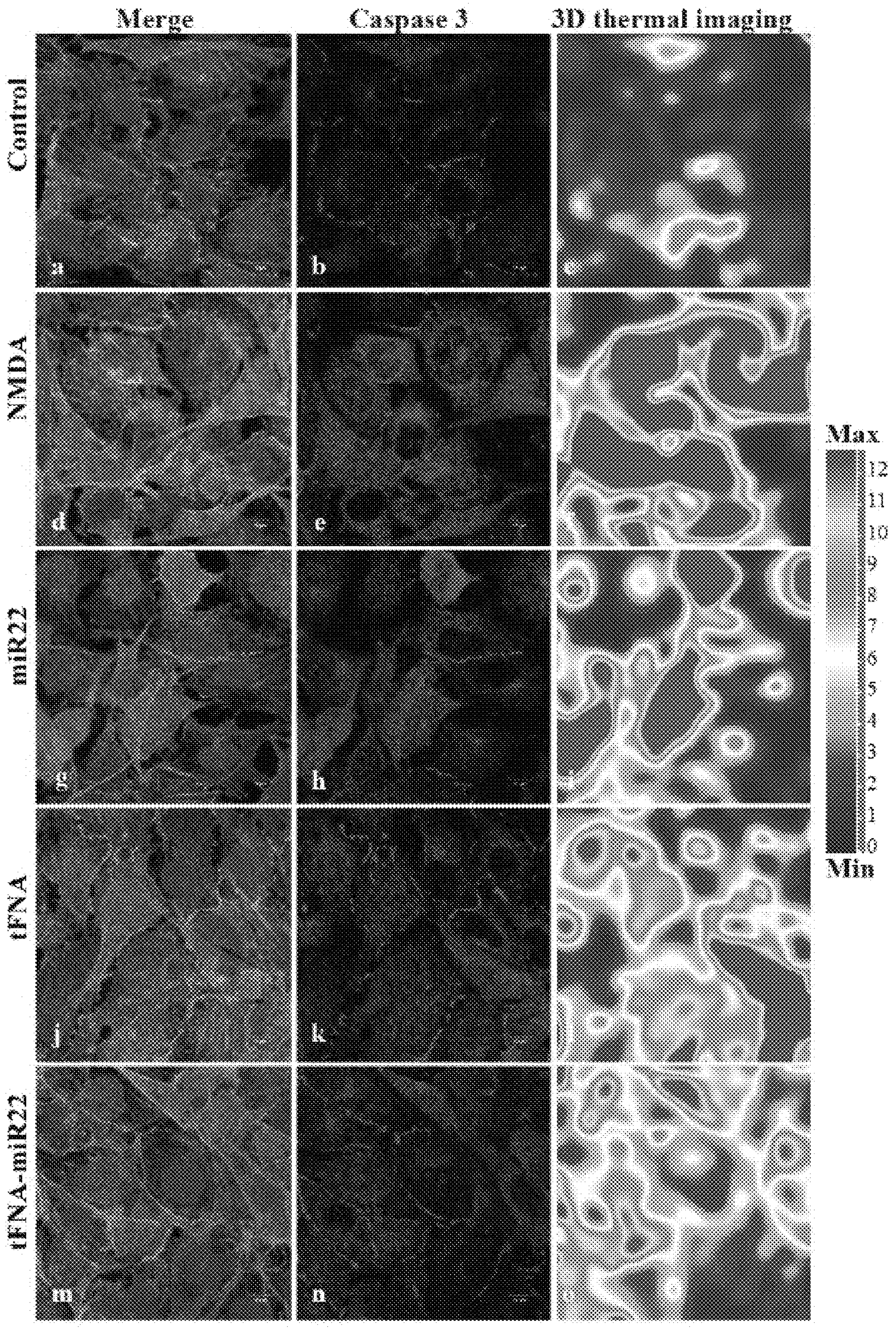
FIG. 17A-B illustrate the immunofluorescence staining (FIG. 17A) of apoptotic protein Caspase-3, and FIG. 17B graphically illustrates a mean fluorescence intensity, and statistical analysis.
Figure 17B:
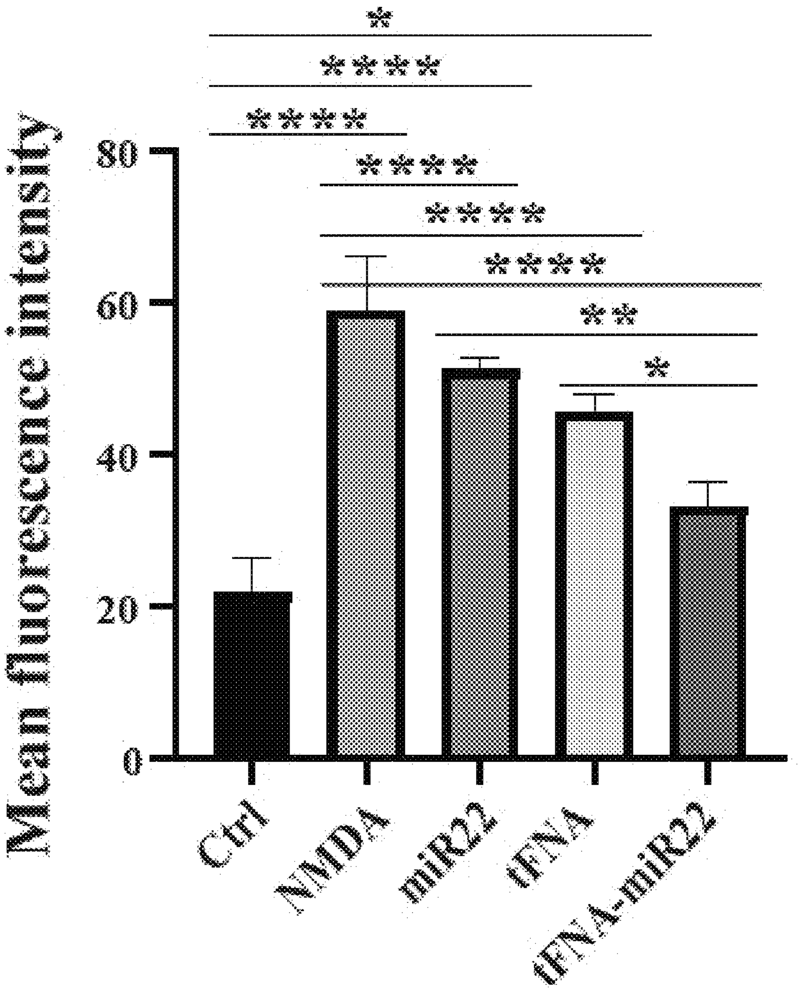

RGC-5 cells treated with 4 mM NIVIDA for 1 h were grouped and then exposed to and treated with Cy5-labeled single-stranded miR-22 (62.5 nM) and tFNA-miR22 (62.5 nM) for 3 h, 6 h, 12 h, and 24 h, respectively, and compared with the injured group (i.e., untreated with tFNA and tFNA-miR22). All groups were washed 3 times with phosphate buffer and detected with flow cytometry. It was found that the fluorescence intensity of tFNA-miR22 reached its peak at 6 h (FIG. 11). Therefore, RGC-5 cells treated for 6 h by the above method were selected to prepare cell slides, and the uptake of single-stranded miR-22 and tFNA-miR22 was observed by immunofluorescence staining.

2. Results

As shown in FIGS. 10-11, the results of cell flow cytometry showed that within 24 h, the fluorescence intensity of tFNA-miR22 reached a peak of 55.3% at 6 h, and gradually decreased to 40.4% with the increase of treatment time, while the fluorescence intensity of single-stranded miR-22 increased slowly with the treatment time, and reached a peak of 33.5% at 24 h. The results of immunofluorescence staining in FIG. 11 showed that tFNA-miR22 was widely accumulated in the cytoplasm and perinuclear of RGC-5 at 6 h, while single-stranded miR-22 mainly adhered to the surface of cell membranes.

The above results indicate that tFNA-miR22 can be taken up more rapidly and efficiently by injured RGC-5 cells, while miR-22 that is not attached to tFNA is difficult to be taken up by RGC-5 cells.

Experimental Example 2. tFNA-miR22 Inhibits NMDA-Induced Cell Injury

1. Experimental Methods

RGC-5 cells were treated with 4 mM NMDA for 1 h, and then treated with 62.5 nM single-stranded miR-22, tFNA or tFNA-miR22 for 24 h, and detected as follows:

1) Cell morphology was observed by phase contrast microscope;
2) Cell cycle was detected by flow cytometry;
3) Cell apoptosis rate was detected by flow cytometry;
4) Expression of Bax, caspase-3 and Bcl-2 was detected by immunofluorescence and Western blot.

2. Results

Figure 6A:
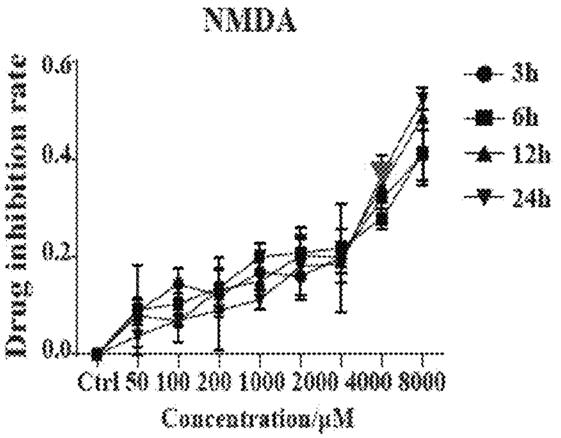
FIG. 6A-E illustrate the establishment of in vivo and in vitro modeling of optic nerve injury by NMDA and the detection results of cell activity of the NMDA-treated retinal ganglion cells with different concentrations of tFNA-miR22.
Figure 6B:
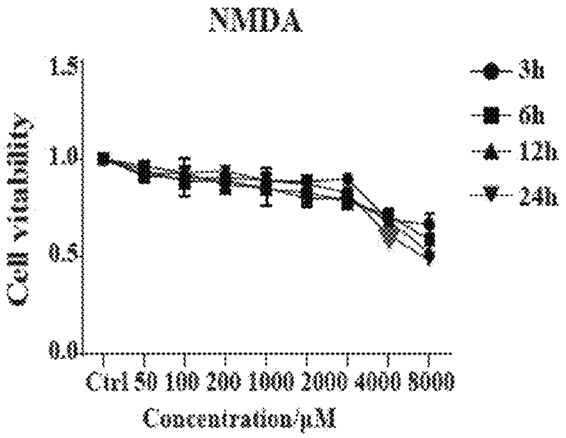
Figure 6C:
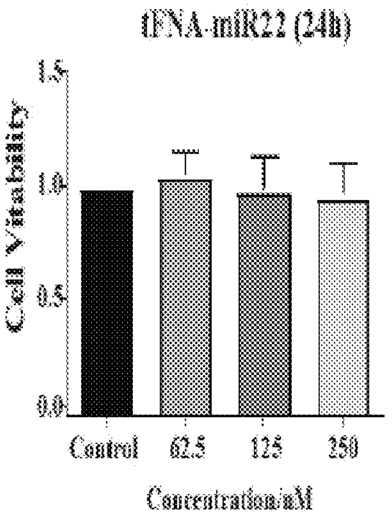
Figure 6D:
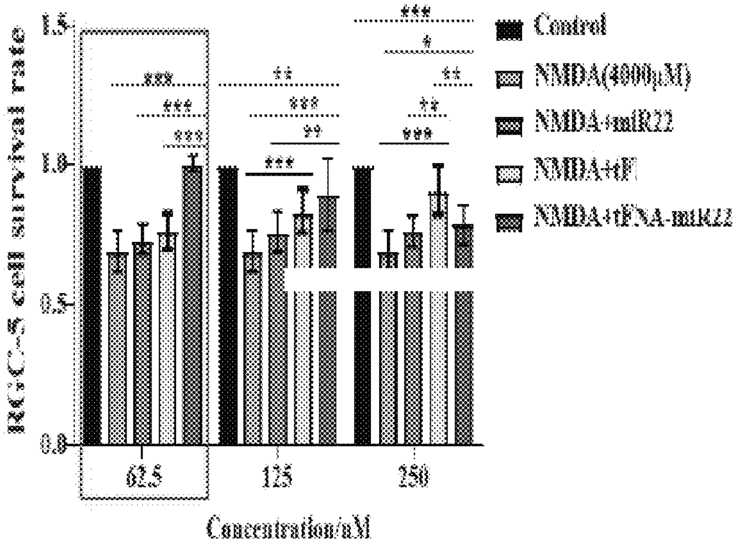

1) FIG. 6C showed that tFNA-miR22 had no significant cytotoxicity, indicating that tFNA-miR22 has good biological safety.

Figure 6E:
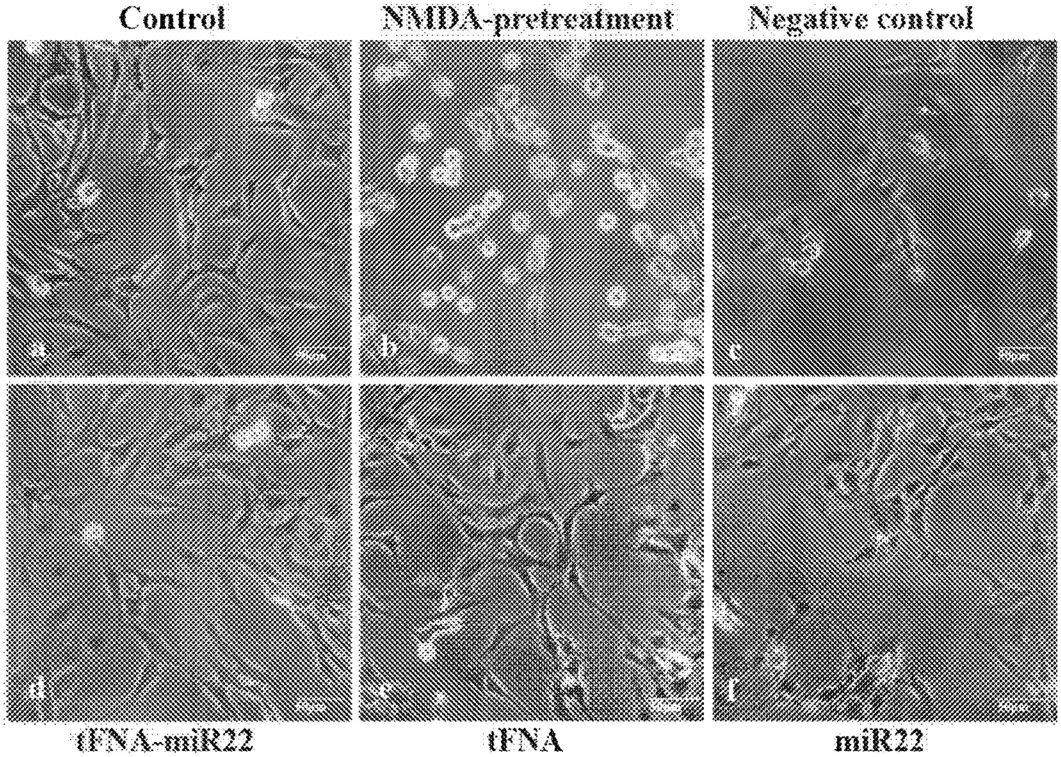
Figure 7:
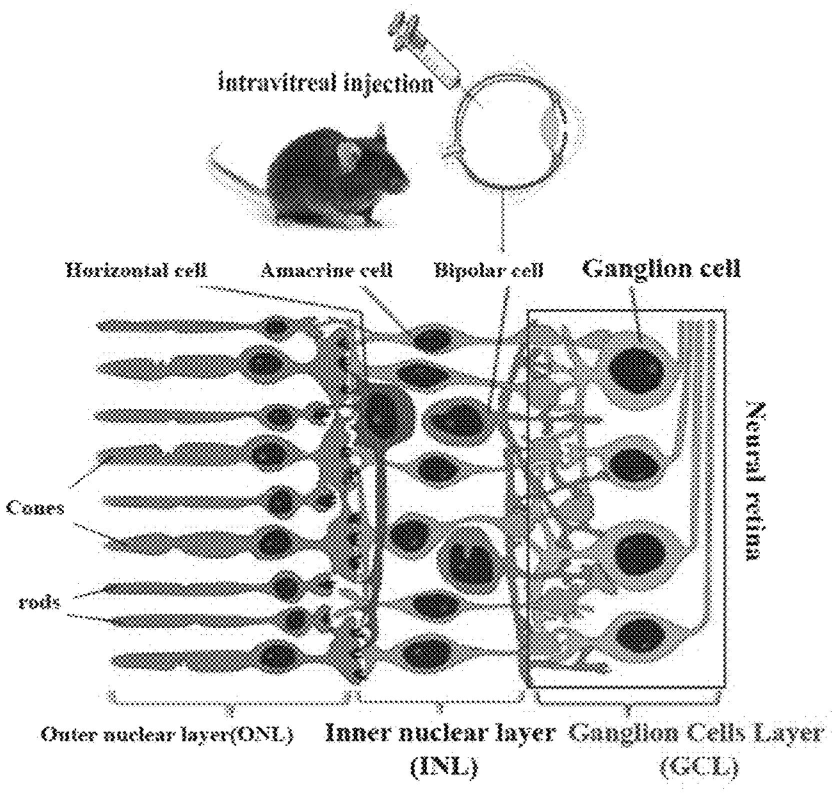
FIG. 7 schematically illustrates a diagram of the establishment of an in vivo model.

2) FIG. 6E shows that compared with tFNA and single-stranded miR-22, tFNA-miR22 can significantly protect the morphology of retinal ganglion cells.

3) FIG. 12 shows that compared with tFNA and single-stranded miR-22, tFNA-miR22 can significantly promote cell self-renewal by regulating cell mitosis; and it can be clearly seen that the mitosis of the NMDA-treated cells was affected, and compared with the control group, the percentage of cells in G2-M phase in the NMDA group significantly decreased; and after the treatment with tFNA or miR22 alone, the percentage of cells in G2-M phase even further decreased. However, after the treatment with tFNA-miR22, the percentage of cells in G2-M phase significantly increased, even comparable to the control group without NMDA interference. It can be seen that the combination of tFNA and miR-22 had an opposite effect compared with use of them alone. They can synergize with each other to significantly promote cell mitosis and self-renewal.

4) FIG. 13-17 showed that tFNA-miR22 can inhibit NMDA-induced apoptosis compared with tFNA or single-stranded miR-22, i.e., tFNA-miR22 can reduce the NMDA-induced up-regulated expression level of apoptosis protein caspase-3 and Bax, and reduce the NMDA-induced down-regulated expression level of anti-apoptosis protein BCL-2.

The above results indicate that tFNA-miR22 has good biosafety and protective effect on retinal ganglion cells. tFNA-miR22 can regulate cell mitosis, promote cell self-renewal, and can reduce the expression of pro-apoptotic proteins caspase-3 and Bax by increasing the expression of anti-apoptosis protein BCL-2, thereby reducing the cell injury caused by NMDA, so as to further play a role in cell protection, and has a significantly better effect than tFNA or single-strand miR-22 alone.

Experimental Example 3. Effect of tFNA-miR22 on TrkB/BDNF Signaling Pathway

1. Experimental Methods

RGC-5 cells were treated according to the method of Experimental example 2, and detected as follows:

1) BDNF and Trkb proteins were detected by Western blot and immunofluorescence;
2) Expression levels of BDNF and Ntrk2 were detected by RT-PCR;
3) ERK1/2, p-ERK1/2, CREB and p-CREB proteins were detected by Western blot and immunofluorescence.

2. Results

Figure 18A:
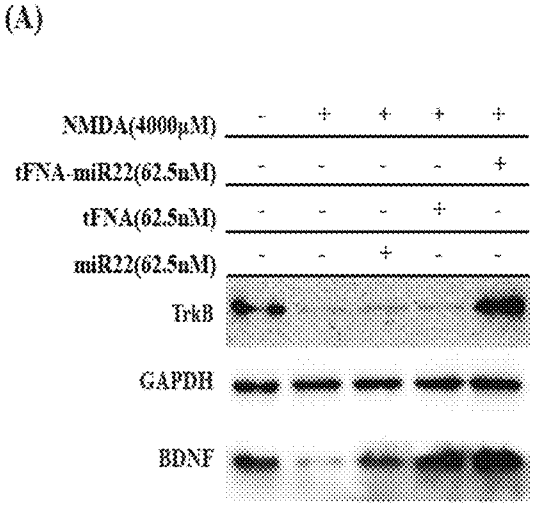
FIG. 18A-E illustrate the relevant detection of TrKb-Creb-BDNF signaling pathway.
Figure 18B:
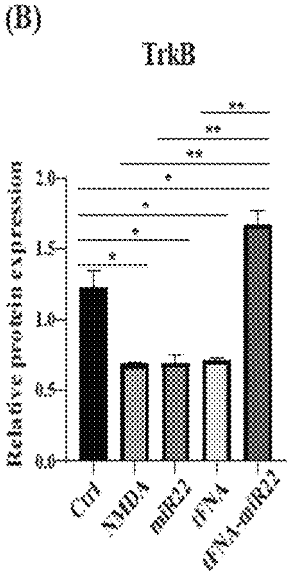
Figure 18C:
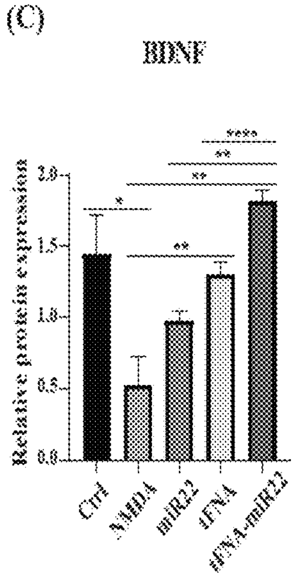
Figure 18D:
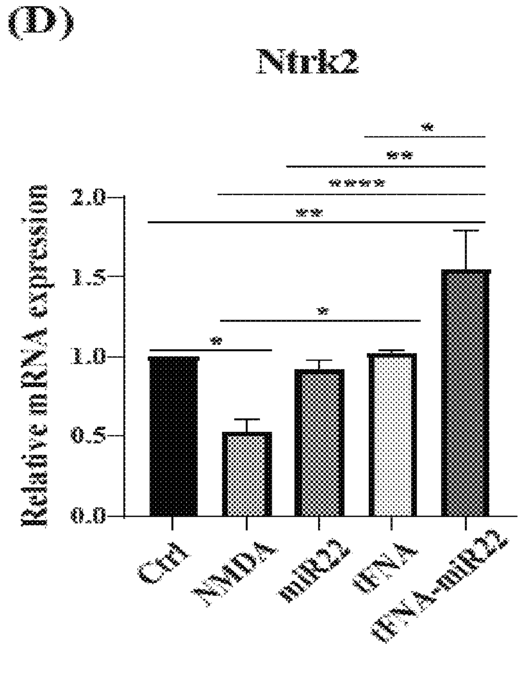
Figure 18E:
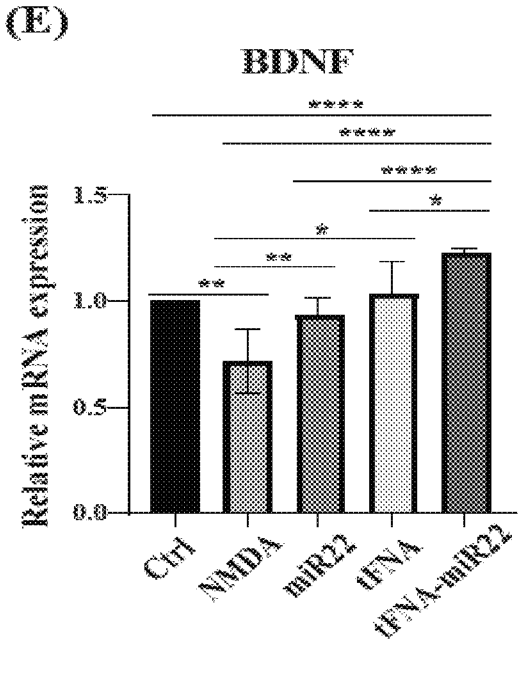

1) The detection of Western blot in FIG. 18A-C showed that the levels of BDNF and TrkB were significantly increased in tFNA-miR22-treated cells. Real-time quantitative PCR results in FIG. 18D-E showed that the gene expression of Ntrk2 and BDNF were significantly increased in tFNA-miR22-treated cells compared with the rest of the groups.

Figure 19A:
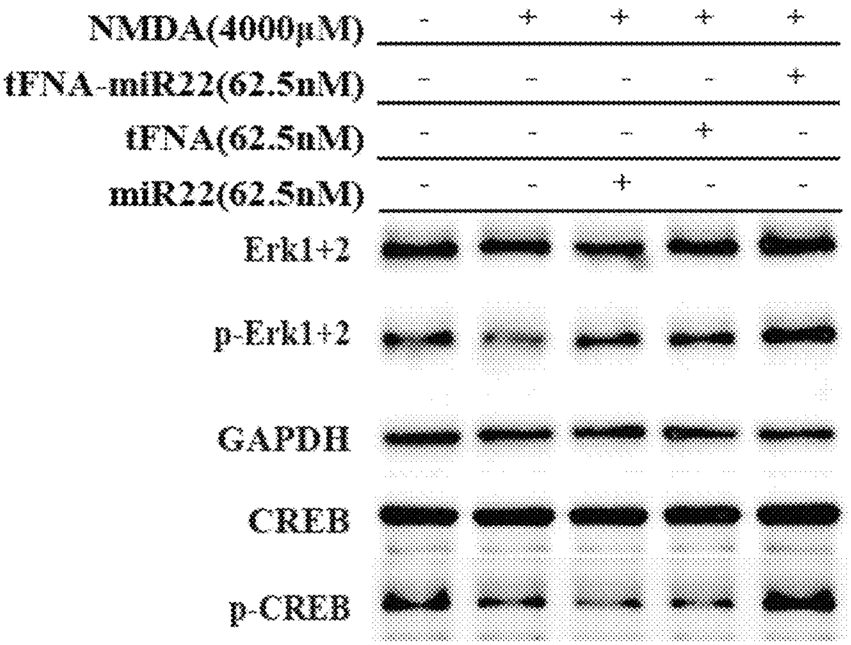
FIG. 19A-C illustrate
Figure 19B:
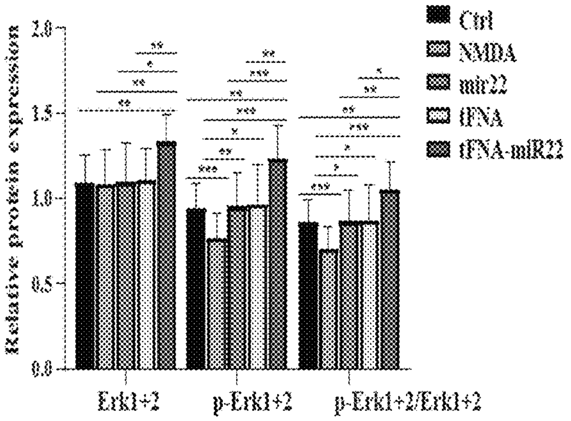
Figure 19C:
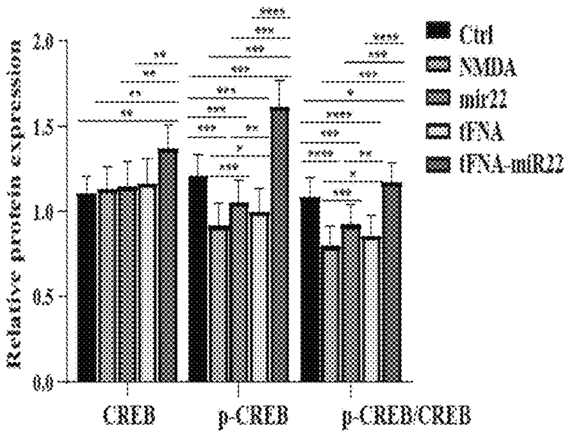
Figure 20A:
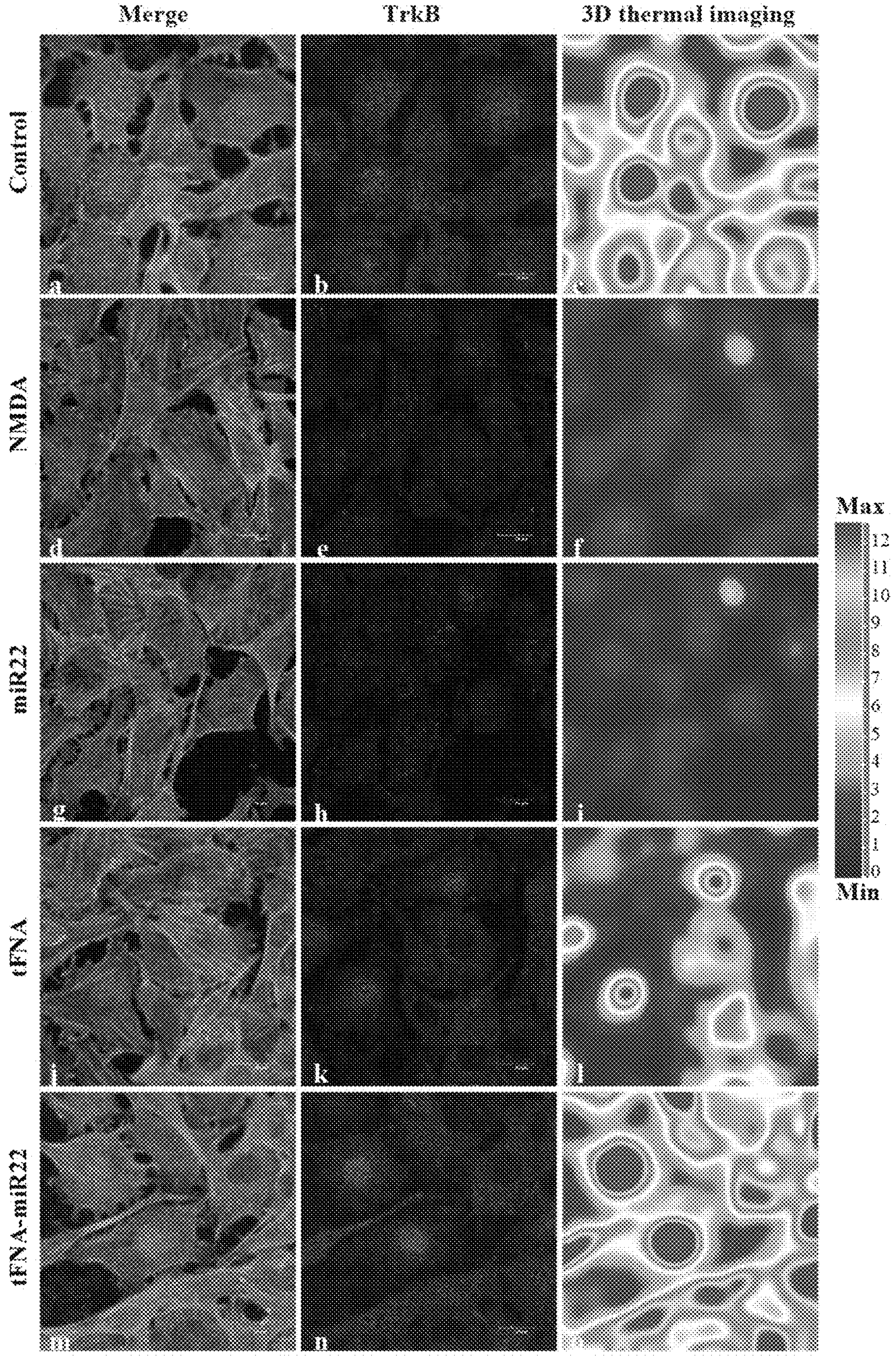
FIG. 20A-B illustrate shews the expression of TrkB selectively activated by tFNA-miR22 detected by immunofluorescence (FIG. 20A), and FIG. 20B graphically illustrates a mean fluorescence intensity, and statistical analysis.
Figure 20B:
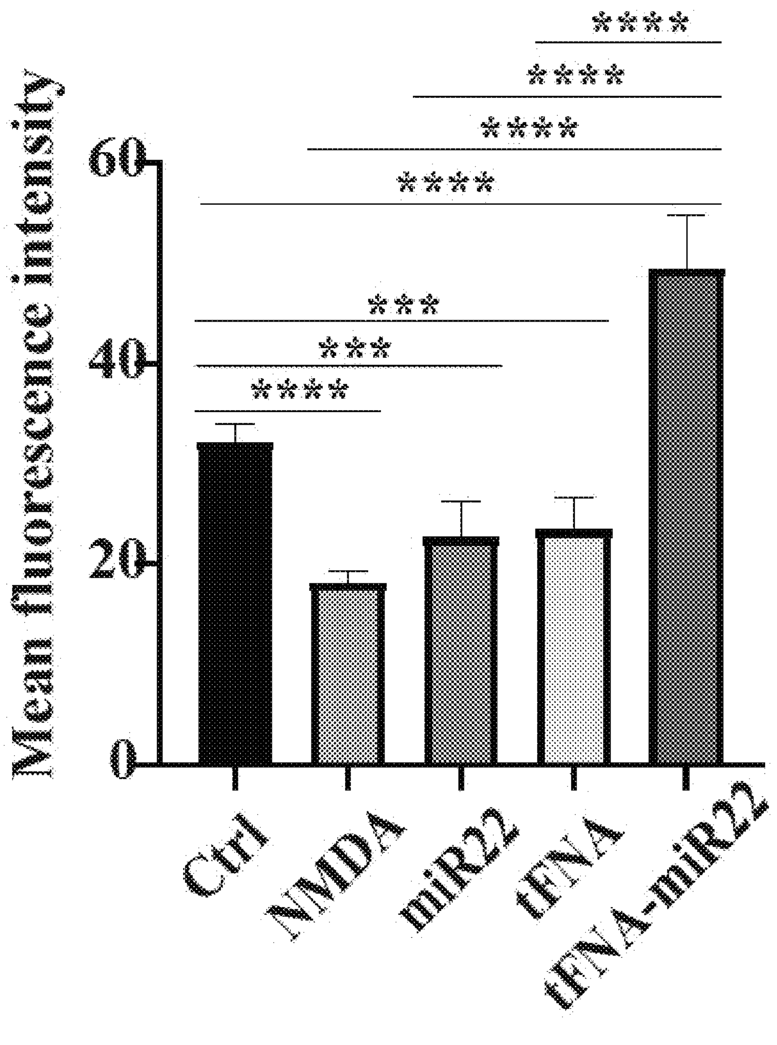
Figure 21A:
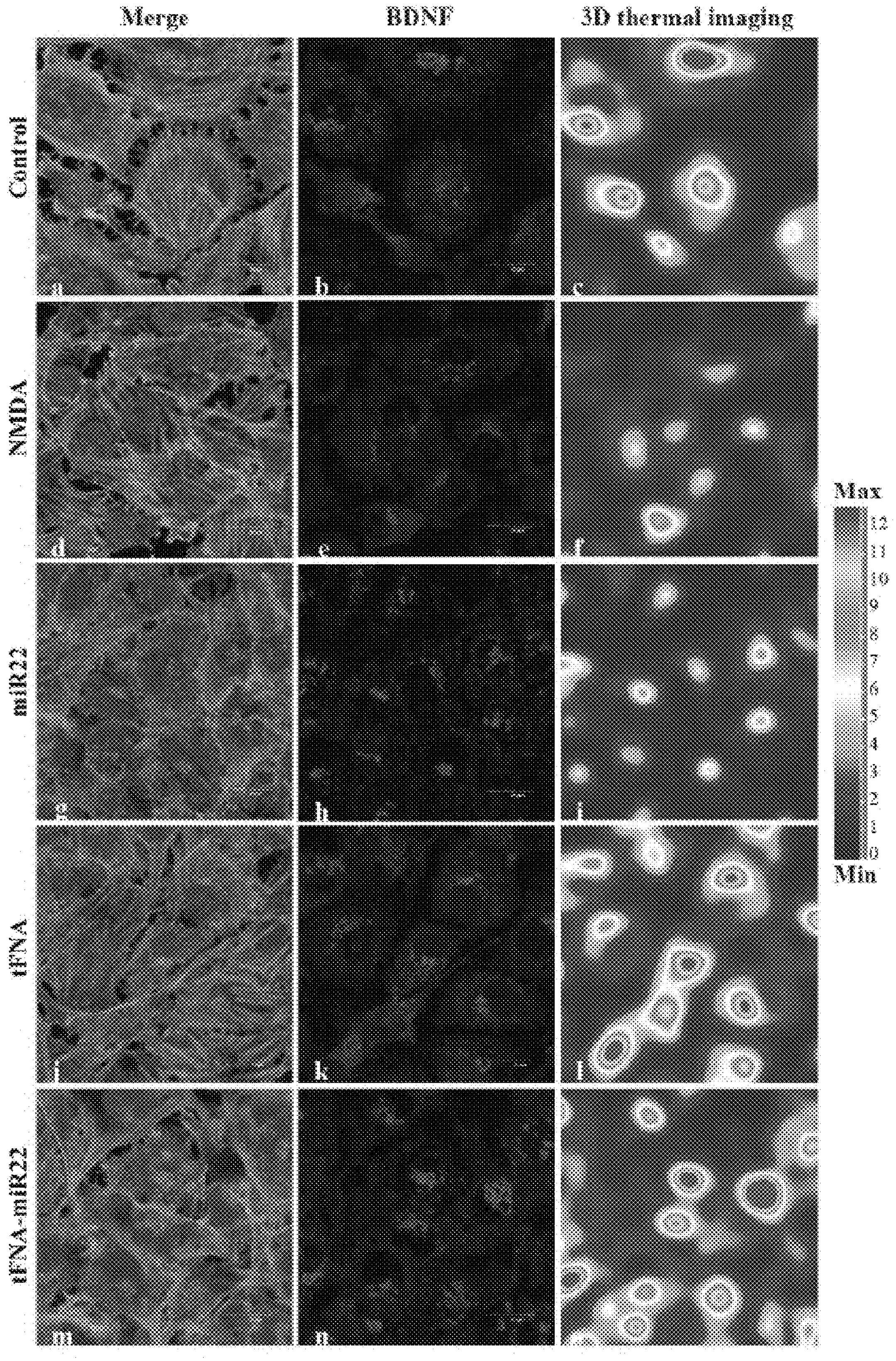
FIG. 21A-B illustrate the expression of BDNF detected by immunofluorescence (FIG. 21A), and FIG. 21B graphically illustrates a mean fluorescence intensity, and statistical analysis.
Figure 21B:
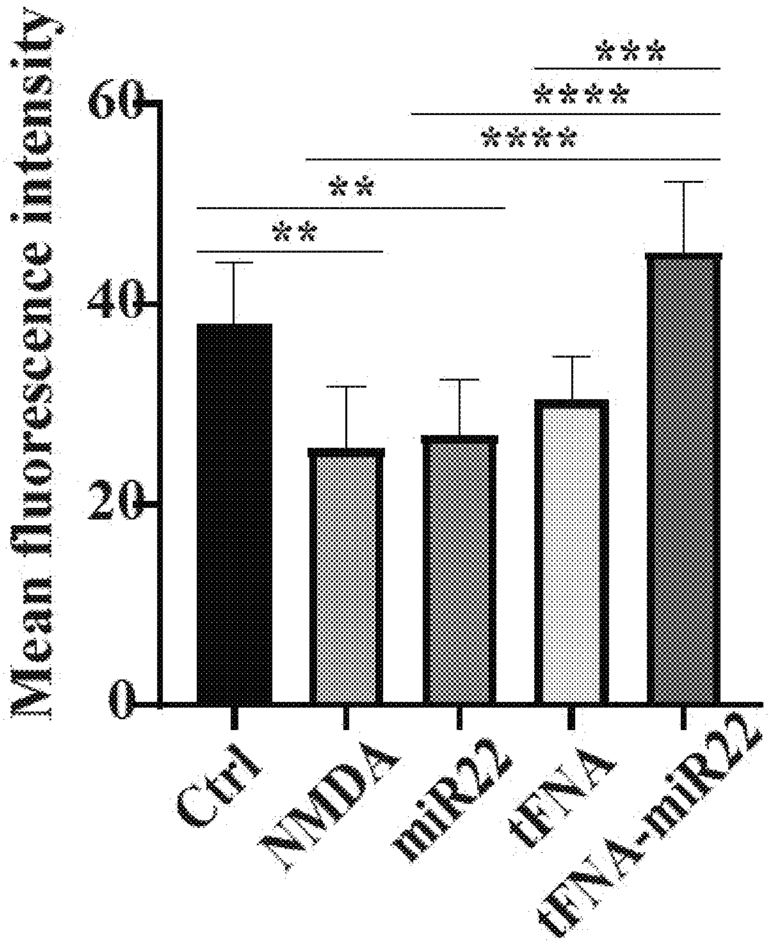
Figure 22A:
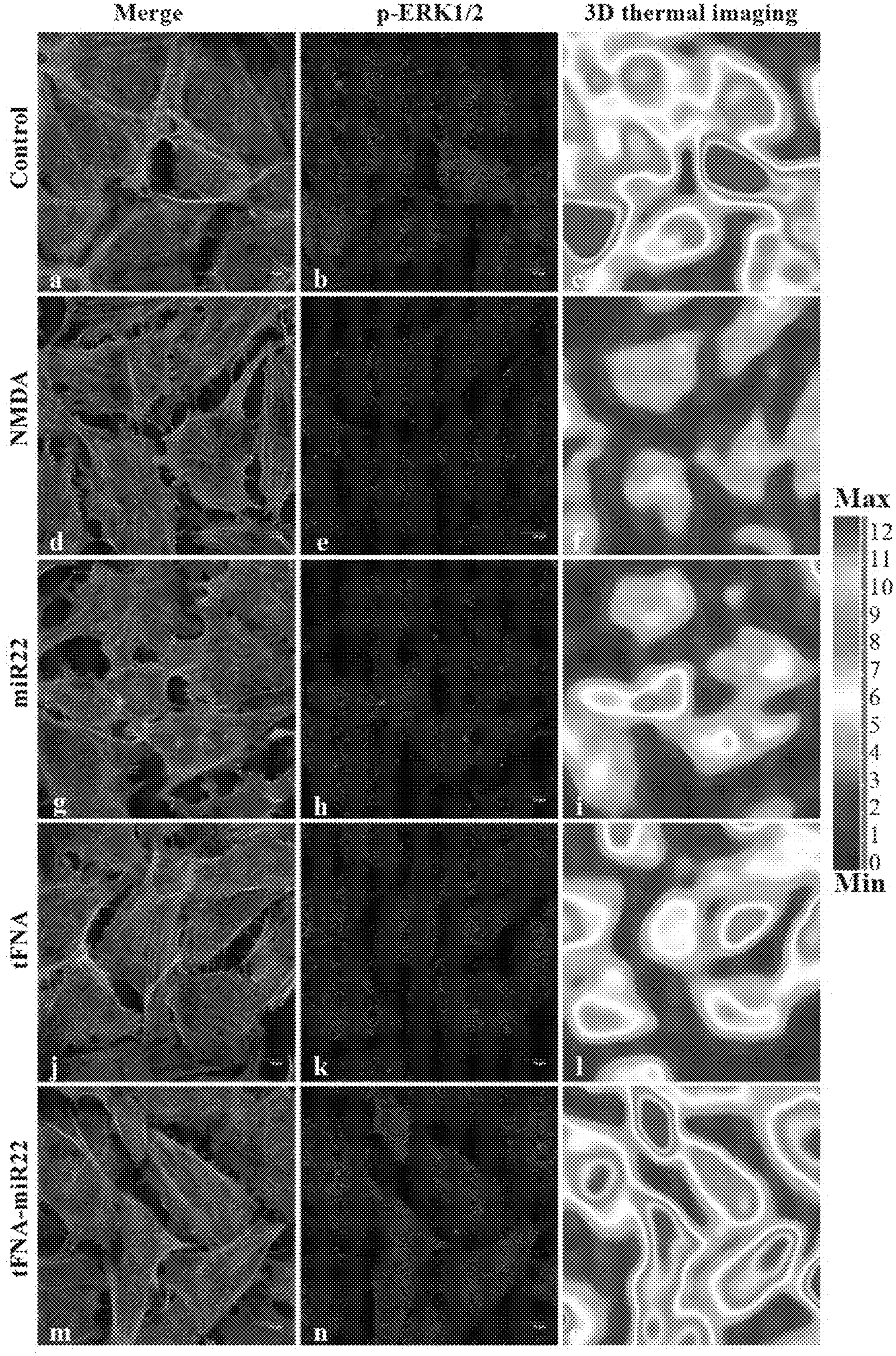
FIG. 22A-B illustrate the expression of p-ERK1/2 detected by immunofluorescence (FIG. 22A), and FIG. 22B graphically illustrates a mean fluorescence intensity, and statistical analysis.
Figure 22B:
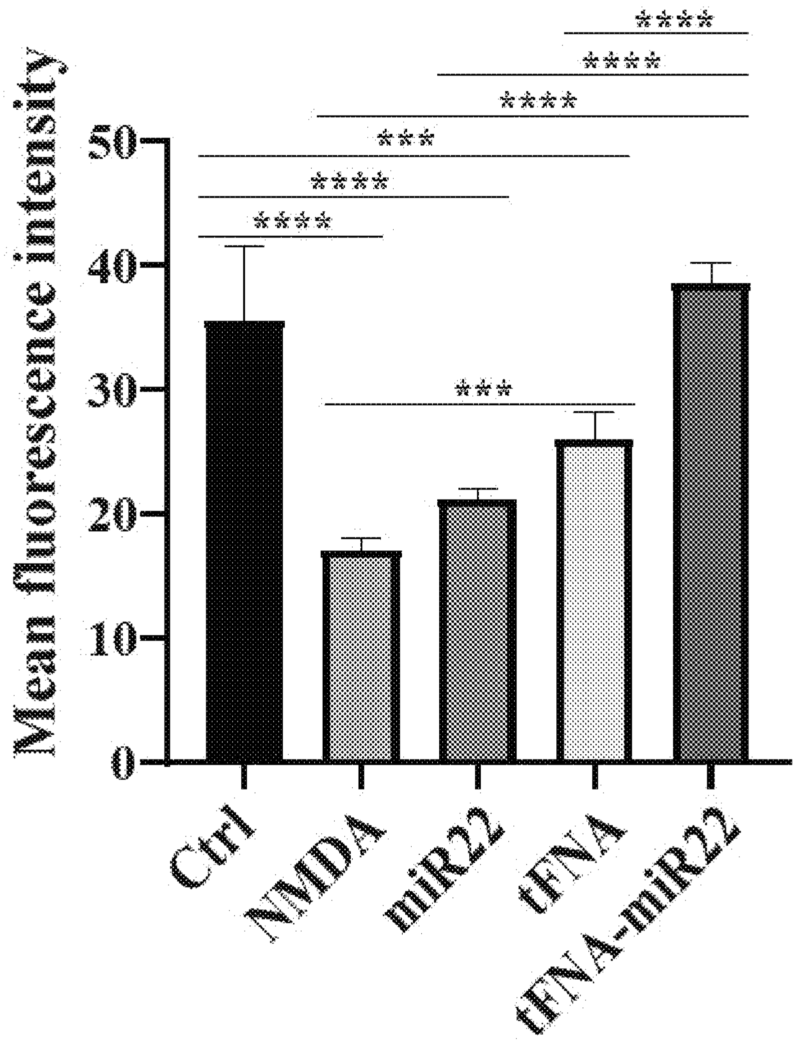
Figure 23A:
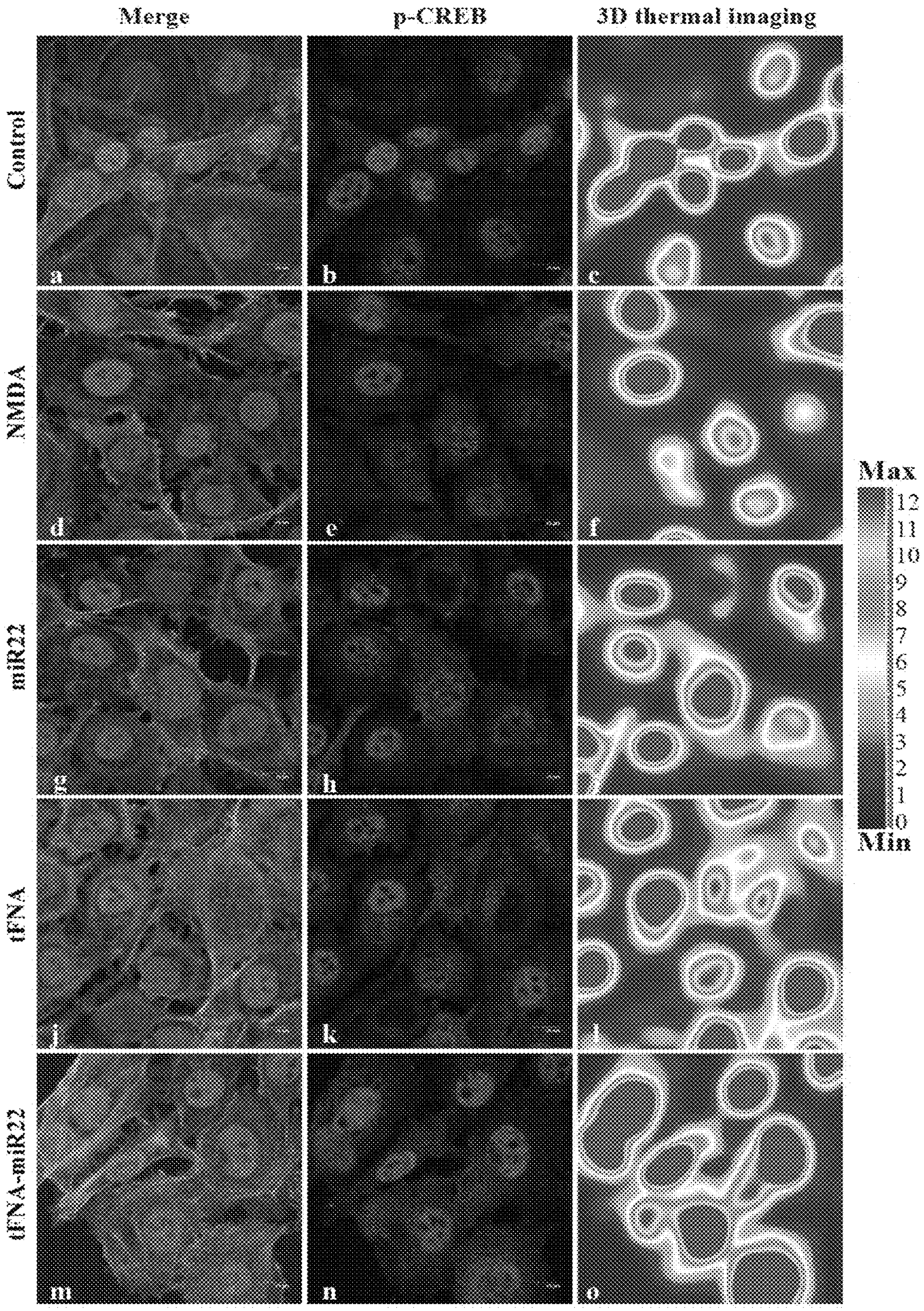
FIG. 23A-B illustrate the expression of p-CREB detected by immunofluorescence (FIG. 23A), and FIG. 23B graphically illustrates a mean fluorescence intensity, and statistical analysis.
Figure 23B:
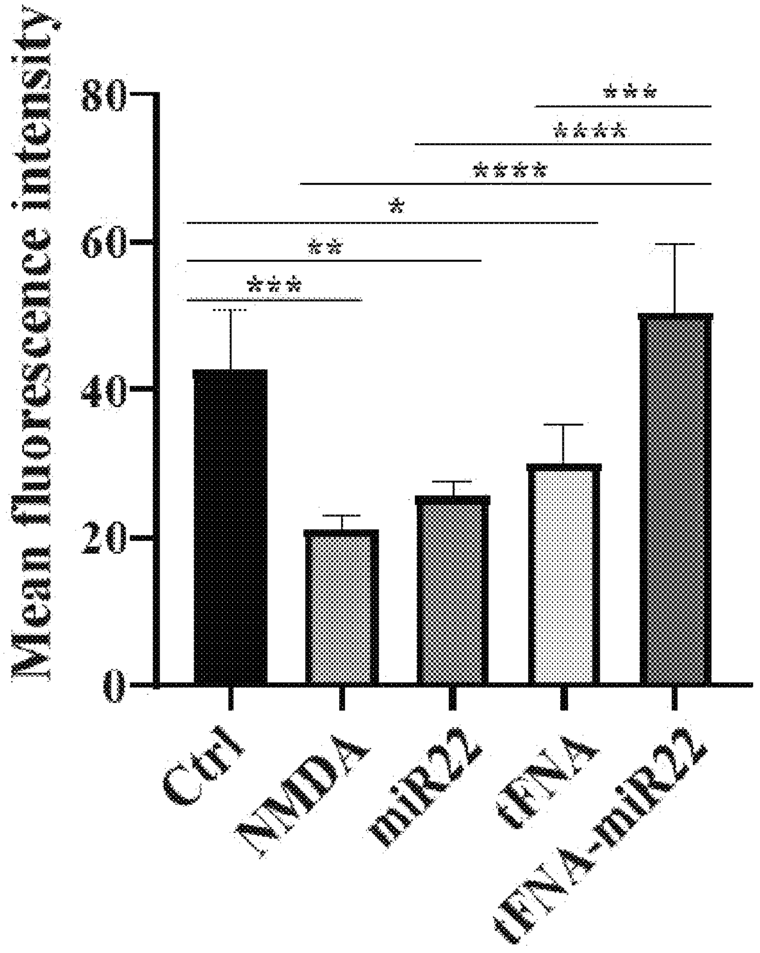

2) The detection of Western blot in FIG. 19 showed that the total proteins of ERK and CREB in tFNA-miR22-treated cells were increased to a certain extent, and could promote the phosphorylation of ERK1/2 and CREB.

3) The detection results of immunofluorescence of the above proteins shown in FIGS. 20-23 were consistent with the detection results of Western blot.

The purpose of this experimental example is to further confirm the mechanism of tFNA-miR22 in producing protective effect on optic nerve.

Brain-derived growth factor (BDNF) is a powerful neuroprotective agent, especially for retinal ganglion cells. BDNF is one of the key neurotrophic factors in glaucoma. By binding to its receptor TrkB, BDNF may activate the extracellular signal-regulated kinase (ERK), which leads to the phosphorylation of cAMP response element-binding protein (CREB), thereby inducing the transcription of various genes associated with neuronal survival and promoting cell survival.

The above results indicate that tFNA-miR22 selectively activates TrkB, and by activating the downstream signaling pathway (ERK-CREB), promotes the release of BDNF to reduce cell injury and promote cell survival.

Experimental Example 4: Treatment of NMDA-Induced Optic Nerve Injury Model Mice with tFNA-miR22

1. Experimental Methods:

Establishment of NMDA-Induced Optic Nerve Injury Model

1) Selection and grouping of experimental animals: The experimental subjects were 6-week-old healthy male C57BL/6J mice, weighing 18-20 g. After examination, there was no obvious crooked neck, the cornea was transparent, the iris blood vessels were clear, the pupils were large and round, and they were sensitive to light reflection. The experimental animals were randomly divided into five ABCDE groups by random number table method, which were blank control group, NMDA injury group, tFNA alone treatment group (62.5 nM), miR-22 alone treatment group and tFNA-miR22 treatment group (62.5 nM), respectively.

(2) Group treatment: After the mice were satisfactorily anesthetized, both eyes of the mice in each group were taken as experimental eyes and the eye surface was disinfected with 10% tincture of iodine. Under the surgical microscope, a 32 G needle was punctured at 1 mm from the temporal temporalis margin of the horn sclera, and then 2 μL drug was injected into the vitreous cavity with a 10 μL microsyringe. Group A: normal mice without surgery; Group B: injected with 2 μL of NMDA prepared in saline at a final concentration of 20 μM; Group C: injected with 1 μL of NMDA (20 μM)+1 μL of tFNAs (62.5 nM); Group D: injected with 1 μL of NMDA (20 μM)+1 μL of miR-22 (62.5 nM); Group E: injected with 1p L NMIDA (20 μM)+1 μL tFNAs-miR22 (62.5 nM). After the operation, erythromycin ophthalmic ointment was applied to the conjunctival sac. The animals were sacrificed 7 days after the operation to remove the eyeball with a section of the optic nerve retained. The following morphological tests were carried out:

A) Retinal histological changes were observed by HE staining;
B) Immunofluorescence staining of whole retinal flat-mounts: RGCs counting;
C) Expression of BDNF and Tkrb was observed by immunohistochemical IHC staining of routine retinal sections.

2. Results

Figures 8A, 8B, 8C, 8D, 8E:
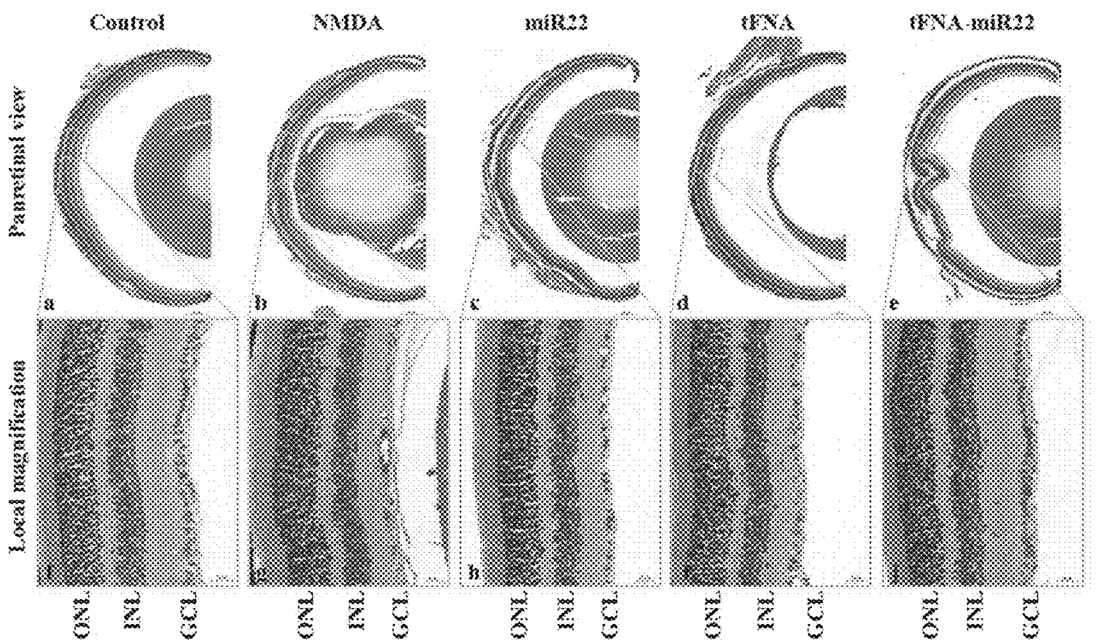

1) The results of HE staining in FIG. 8 showed that after tFNAs-miR22 treatment, the retinal thickness increased significantly and the number of ganglion cells increased significantly.

Figure 9A:
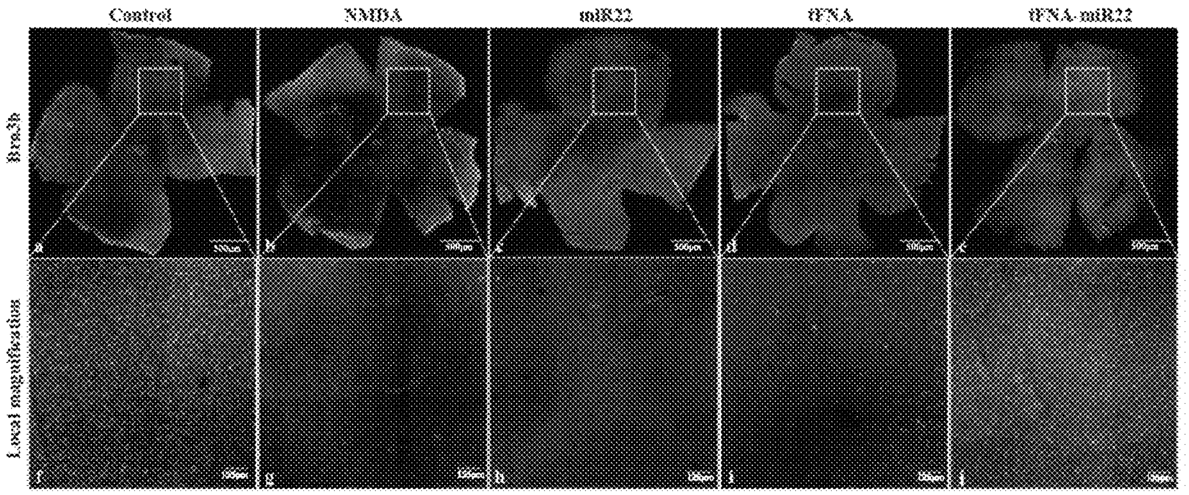
FIG. 9A-B shows the images of immunofluorescence staining of retinal flat-mounts and data analysis (FIG. 9A), and FIG. 9B graphically illustrates the data of FIG. 9A, and the data refer to mean±standard deviation (with sample size of each group ≥3).
Figure 9B:
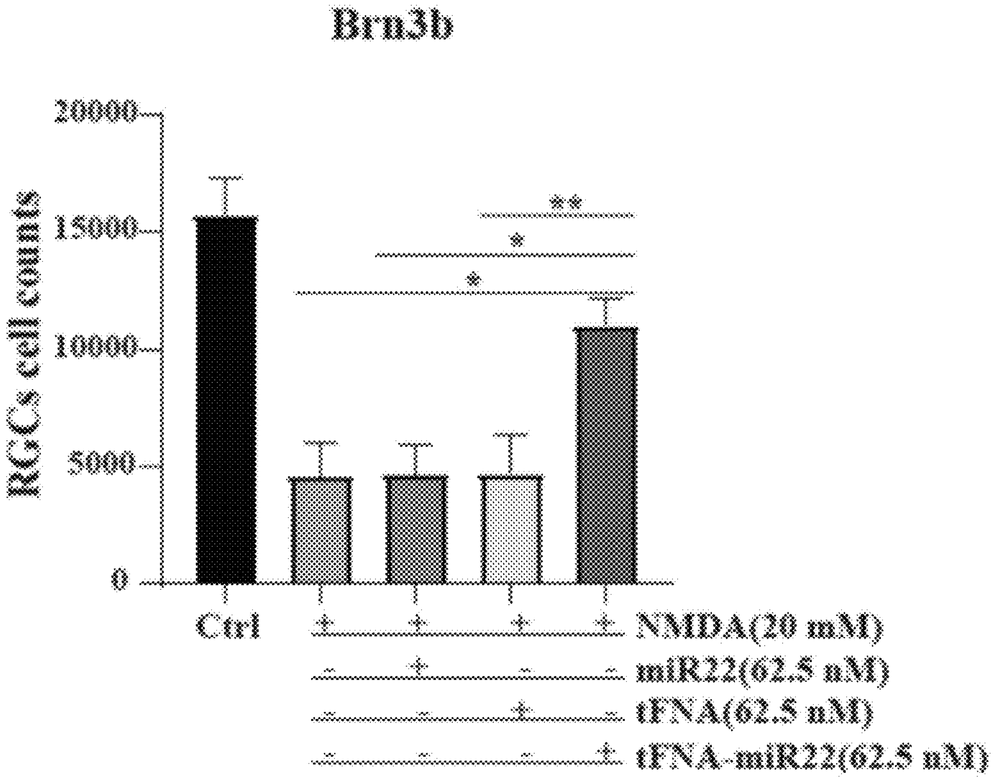

2) The immunofluorescence staining results of the flat-mounts are shown in FIG. 9.: After tFNAs-miR22 treatment, the number of ganglion cells increased significantly, with statistical significance; the number of ganglion cells in tFNA-miR22 treatment group significantly increased compared with the NMIDA control group, while the number of ganglion cells after treated with tFNA or miR22 alone was almost unchanged compared with the NMDA treatment group.

Figure 24A:
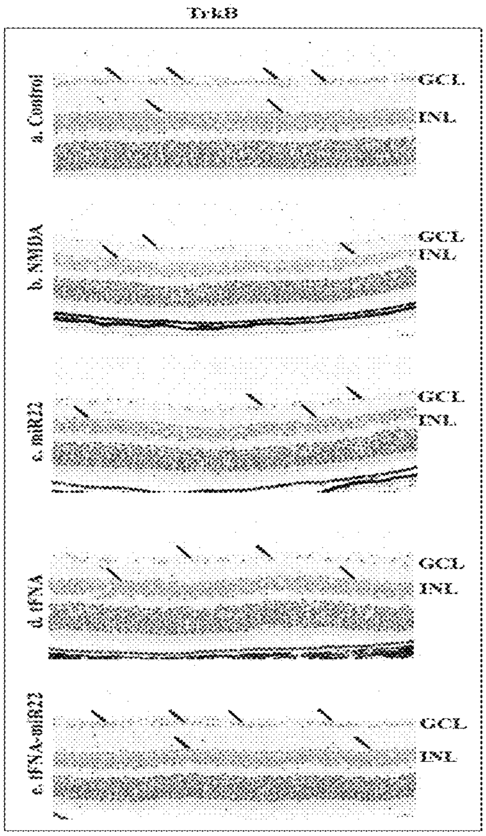
FIG. 24A-B illustrate the expression results of TrkB protein FIG. 24A and BDNF protein FIG. 24B by immunohistochemical staining.
Figure 24B:
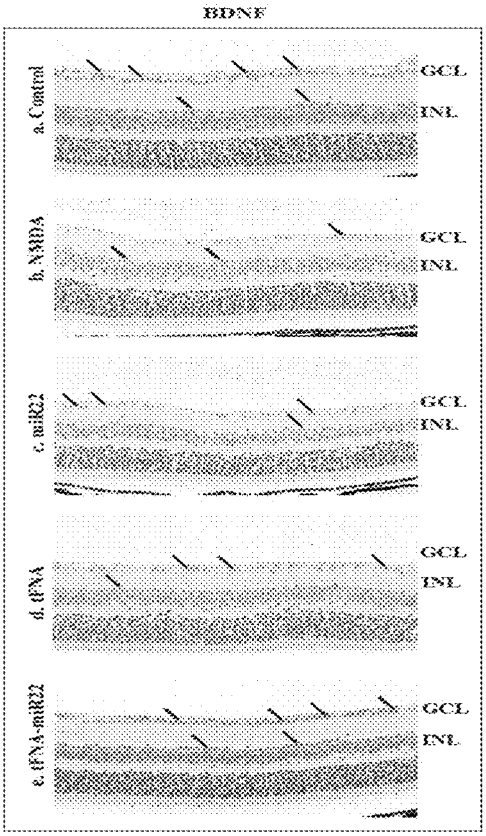

3) IHC staining results are shown in FIG. 24.: After tFNAs-miR22 treatment, the expressions of BDNF and Tkrb in the retina were significantly increased.

It can be concluded that the tFNA-miR22 group significantly increased the survival rate of optic ganglia cells compared with the other groups, indicating that the complex tFNA-miR22 of the present invention has an optic nerve protective effect, and can be used in the treatment of neurodegenerative optic nerve diseases including glaucoma; and has a significantly better effect than tFNA and miR-22 alone, indicating that the two have a synergistic effect.

In summary, the present invention provides a neuroprotective drug that can be used to treat neurodegenerative optic nerve diseases including glaucoma, which comprises tFNA-miR22 composed of a tetrahedral DNA and a miR-22 in a molar ratio of 1:(1-4). tFNA-miR22 can not only be effectively taken up by injured RGC-5 cells, but also effectively inhibit the apoptosis of retinal ganglion cells, and promote the release of brain-derived nerve factor (BDNF), thereby playing a good protective effect on retinal ganglion cells.

The invention claimed is:

1. A product of manufacture or formulation comprising a tetrahedral DNA covalently linked to a miR-22 by an oligonucleotide linker moiety, wherein:

the tetrahedral DNA comprises 4 single-stranded DNAs in tetrahedral spacial relationship formed by complementary base pairing of the 4 single-stranded DNAs, the miR-22 has a sequence as set forth in SEQ ID NO:5;

the 4 single-stranded DNAs have a sequence as set forth in SEQ ID NO:1, SEQ ID NO:2, SEQ ID NO:3, and SEQ ID NO:4, respectively, one of the four tetrahedral DNA is covalently linked to the miR-22 by the oligonucleotide linker moiety, the oligonucleotide linker moiety has a sequence comprising TTTTT.

2. A method for making the product of manufacture or formulation of claim 1, comprising putting the four single-stranded DNAs forming the DNA tetrahedron at a temperature sufficient to denature them for more than 10 min, and then reducing the temperature to 2-8° C. for more than 20 min, wherein one or more of the 4 single-stranded DNAs are linked to the miR-22.

3. The preparation method of claim 2, wherein the method comprises putting the four single-stranded DNAs forming the DNA tetrahedron at 95° C. for 10 min, and reducing the temperature to 4° C. for 20 min.

4. A pharmaceutical composition comprising a product of manufacture or formulation of claim 1 and a pharmaceutically acceptable excipient.

5. A method of treating an optic nerve injury comprising a glaucoma-associated optic neuropathy or caused by retinal ganglion cell apoptosis, comprising administrating a pharmaceutical composition of claim 4 to an individual in need thereof.

6. A method for treating an optic nerve injury comprising a glaucoma-associated optic neuropathy or caused by retinal ganglion cell apoptosis, comprising administering the pharmaceutical composition of claim 4 to the individual in need thereof.

7. A method for treating glaucoma in an individual in need thereof, comprising administering the pharmaceutical composition of claim 4 the individual in need thereof.

8. The method of claim 5, wherein the optic nerve injury comprises a retinal ganglion cell injury.

9. The method of claim 5, wherein the optic nerve injury is associated with the regulation of a brain-derived neurogenic factor-related signaling pathway.

10. The method of claim 5, wherein the optic nerve injury is a glaucoma-associated optic neuropathy.

11. The method of claim 6, wherein the optic nerve injury is a glaucoma-associated optic neuropathy.

12. The method of claim 6, wherein the formulation is injected into a vitreous cavity of an eye.

13. The method of claim 7, wherein the formulation is injected into a vitreous cavity of an eye.

14. The product of manufacture or formulation of claim 1, formulated for injection.

15. The product of manufacture or formulation of claim 14, formulated for injection into a vitreous cavity of an eye.

16. A method for promoting retinal ganglion cell survival in an individual in need thereof, comprising administering the pharmaceutical composition of claim 4, to the individual in need thereof.

17. A method for treating an optic nerve injury comprising glaucoma in an individual in need thereof, comprising administering the product of manufacture or formulation of claim 1 to the individual in need thereof.

18. The method of claim 17, wherein the optic nerve injury is associated with a retinal ganglion cell apoptosis.

19. A method for treating an optic nerve injury comprising a glaucoma-associated optic neuropathy or caused by retinal ganglion cell apoptosis in an individual in need thereof, comprising administering the product of manufacture or formulation of claim 1 to the individual in need thereof.

20. The product of manufacture or formulation of claim 1, wherein SEQ ID NO:3, one of the four tetrahedral DNA, is the DNA covalently linked to the miR-22 by the oligonucleotide linker moiety.

* * * * *